United States Patent
Ye

(10) Patent No.: US 9,724,429 B2
(45) Date of Patent: Aug. 8, 2017

(54) PROMOTERS, EXPRESSION CASSETTES, VECTORS, KITS, AND METHODS FOR THE TREATMENT OF ACHROMATOPSIA AND OTHER DISEASES

(71) Applicant: Guo-Jie Ye, Gainsville, FL (US)

(72) Inventor: Guo-Jie Ye, Gainsville, FL (US)

(73) Assignee: Applied Genetic Technologies Corporation, Alachua, FL (US)

( * ) Notice: Subject to any disclaimer, the term of this patent is extended or adjusted under 35 U.S.C. 154(b) by 0 days.

(21) Appl. No.: 14/269,723

(22) Filed: May 5, 2014

(65) Prior Publication Data

US 2014/0364486 A1    Dec. 11, 2014

Related U.S. Application Data

(60) Provisional application No. 61/824,071, filed on May 16, 2013.

(51) Int. Cl.
*C12N 15/85* (2006.01)
*A61K 48/00* (2006.01)
*C12N 15/86* (2006.01)

(52) U.S. Cl.
CPC .......... *A61K 48/00* (2013.01); *A61K 48/0058* (2013.01); *C12N 15/86* (2013.01); *C12N 2750/14141* (2013.01); *C12N 2830/008* (2013.01)

(58) Field of Classification Search
None
See application file for complete search history.

(56) References Cited

U.S. PATENT DOCUMENTS

2012/0015841 A1    1/2012   Shekdar et al.
2012/0172419 A1    7/2012   Neitz et al.

FOREIGN PATENT DOCUMENTS

WO    WO-2012/094560 A2    7/2012
WO    WO-2012/145601 A2    10/2012

OTHER PUBLICATIONS

Chang et al., "Cone Photoreceptor Function Loss-3, a Novel Mouse Model of Achromatopsia Due to a Mutation in Gnat2," Investigative Opthamology & Visual Science, vol. 47, No. 11, pp. 5017-5021 (2006).
McClements et al., "Gene therapy for retinal disease," Transl Res, vol. 61, pp. 241-254 (2013).
Parikh et al., "A path towards restoration of vision using ocular gene therapy: An opthalmic review," Int J Pharm Biomed Sci, vol. 3, pp. 140-147 (2012).
Li, Q. et al., "Cone-specific expression using a human red opsin promoter in recombinant AAV." Vision Research, vol. 48, No. 3, pp. 332-338 (2008).
Wang, Y. et al., "A locus control region adjacent to the human red and green visual pigment genes." Neuron, vol. 9, No. 3, pp. 429-440 (1992).

*Primary Examiner* — Antonio Galisteo Gonzalez
(74) *Attorney, Agent, or Firm* — McCarter & English, LLP; Jonathan M. Sparks; Kevin A. Fiala

(57) ABSTRACT

The present invention provides isolated promoters, transgene expression cassettes, vectors, kits, and methods for treatment of genetic diseases that affect the cone cells of the retina.

16 Claims, 12 Drawing Sheets

FIG. 4A

SEQ ID NO: 1:

gtgggaccacaaatgagttttcacctggcctggggacacacgtgcccccacaggtgctgagtgacttctaggacagtaatctgctttaggct aaaatgggacttgatcttctgttagccctaatcatcaattagcagagccggtgaaggtgcagaacctaccgcctttccaggcctcctcccacct ctgccacctccactctccttcctgggatgtgggggctggcacacgtgtggcccagggcattggtgggattgcactgagctgggtcattagcg taatcctggacaagggcagacagggcgagcggagggccagctccggggctcaggcaaggctgggggcttcccccagacaccccactc ctcctctgctggaccccccacttcatagggcacttcgtgttctcaaagggcttccaaatagcatggtggccttggatgcccagggaagcctcag agttgcttatctccctctagacagaaggggaatctcggtcaagagggagaggtcgccctgttcaaggccacccagccagctcatggcggta atgggacaaggctggccagccatcccaccctcagaagggacccggtggggcaggtgatctcagaggaggctcacttctgggtctcacatt cttggatccggttccaggcctcggccctaaatagtctccctgggctttcaagagaaccacatgagaaaggaggattcgggctctgagcagtt tcaccacccaccccccagtctgcaaatcctgacccgtgggtccacctgccccaaaggcggacgcaggacagtagaagggaacagagaa cacataaacacagagagggccacagcggctcccacagtcaccgccaccttcctggcggggatgggtggggcgtctgagtttggttccca gcaaatccctctgagccgcccttgcgggctcgcctcaggagcaggggagcaagaggtgggaggaggaggtctaagtcccaggcccaat taagagatcaggtagtgtagggtttgggagcttttaaggtgaagaggcccgggctgatcccacaggccagtataaagcgccgtgaccctca ggtgatgcgccagggccggctgccgtcggggacagggcttccatagccatg

FIG. 4B

SEQ ID NO: 2:

agccatcggctgttagtgacaaagcccctgagtcaagatgacagcagcccccataactcctaatcggctctcccgcgtggagtcatttagga
gtagtcgcattagagacaagtccaacatctaatcttccaccctggccagggccccagctggcagcgagggtgggagactccgggcagag
cagagggcgctgacattggggcccggcctggcttgggtccctctggcctttccccaggggccctctttccttggggctttcttgggccgcca
ctgctcccgctcctctcccccatccaccccctcacccctcgttcttcatatccttctctagtgctccctccactttcatccaccttctgcaag
agtgtgggaccacaaatgagttttcacctggcctggggacacacgtgcccccacaggtgctgagtgactttctaggacagtaatctgctttag
gctaaaatgggacttgatcttctgttagccctaatcatcaattagcagagccggtgaaggtgcagaacctaccgcctttccaggcctcctccc
acctctgccacctccactctccttcctgggatgtgggggctggcacacgtgtggcccagggcattggtgggattgcactgagctgggtcatt
agcgtaatcctggacaagggcagacagggcgagcggagggccagctccggggctcaggcaaggctgggggcttccccagacaccc
cactcctcctctgctggaccccacttcatagggcacttcgtgttctcaaagggcttccaaatagcatggtggccttggatgcccagggaagc
ctcagagttgcttatctccctctagacagaaggggaatctcggtcaagagggagaggtcgccctgttcaaggccacccagccagctcatgg
cggtaatgggacaaggctggccagccatcccaccctcagaagggacccggtggggcaggtgatctcagaggaggctcacttctgggtct
cacattcttggatccggttccaggcctcggccctaaatagtctccctgggctttcaagagaaccacatgagaaaggaggattcgggctctga
gcagtttcaccacccaccccccagtctgcaaatcctgacccgtgggtccacctgccccaaaggcggacgcaggacagtagaagggaaca
gagaacacataaacacagagagggccacagcggctcccacagtcaccgccaccttcctggcggggatgggtggggcgtctgagtttggt
tcccagcaaatccctctgagccgcccttgcgggctcgcctcaggagcaggggagcaagaggtgggaggaggaggtctaagtcccaggc
ccaattaagagatcaggtagtgtaggggtttgggagcttttaaggtgaagaggcccgggctgatcccacaggccagtataaagcgccgtgac
cctcaggtgatgcgccagggccggctgccgtcggggacagggctttccatagccatg

FIG. 4C

SEQ ID NO: 3:

ggaggctgagggggtggggaaagggcatgggtgtttcatgaggacagagcttccgtttcatgcaatgaaaagagtttggagacggatggtg gtgactggactatacacttacacacggtagcgatggtacactttgtattatgtatattttaccacgatcttttaaagtgtcaaaggcaaatggcca aatggttccttgtcctatagctgtagcagccatcggctgttagtgacaaagcccctgagtcaagatgacagcagcccccataactcctaatcg gctctcccgcgtggagtcatttaggagtagtcgcattagagacaagtccaacatctaatcttccaccctggccagggccccagctggcagc gagggtgggagactccgggcagagcagagggcgctgacattgggccccggcctggcttgggtccctctggcctttccccaggggccct ctttccttggggctttcttgggccgccactgctcccgctcctctcccccatcccaccccctcaccccctcgttcttcatatccttctctagtgctc cctccactttcatccaccttctgcaagagtgtgggaccacaaatgagttttcacctggcctggggacacacgtgcccccacaggtgctgag tgactttctaggacagtaatctgctttaggctaaaatgggacttgatcttctgttagccctaatcatcaattagcagagccggtgaaggtgcaga acctaccgcctttccaggcctcctcccacctctgccacctccactctccttcctgggatgtgggggctggcacacgtgtggcccagggcatt ggtgggattgcactgagctgggtcattagcgtaatcctggacaagggcagacagggcgagcggagggccagctccggggctcaggcaa ggctgggggcttcccccagacaccccactcctcctctgctggaccccacttcatagggcacttcgtgttctcaaagggcttccaaatagcat ggtggccttggatgcccagggaagcctcagagttgcttatctccctctagacagaaggggaatctcggtcaagagggagaggtcgccctgt tcaaggccacccagccagctcatggcggtaatgggacaaggctggccagccatcccaccctcagaagggacccggtggggcaggtgat ctcagaggaggctcacttctgggtctcacattcttggatccggttccaggcctcggccctaaatagtctccctgggctttcaagagaaccacat gagaaaggaggattcgggctctgagcagtttcaccacccaccccccagtctgcaaatcctgacccgtgggtccacctgccccaaaggcgg acgcaggacagtagaagggaacagagaacacataaacacagagagggccacagcggctcccacagtcaccgccaccttcctggcggg gatgggtggggcgtctgagtttggttcccagcaaatccctctgagccgcccttgcgggctcgcctcaggagcaggggagcaagaggtgg gaggaggaggtctaagtcccaggcccaattaagagatcaggtagtgtagggtttgggagcttttaaggtgaagaggcccgggctgatccc acaggccagtataaagcgccgtgaccctcaggtgatgcgccagggccggctgccgtcggggacagggctttccatagccatg

FIG. 4D

SEQ ID NO: 4:

cccctacagcagccagggtgagattatgaggctgagctgagaatatcaagactgtaccgagtaggggggccttggcaagtgtggagagcc
cggcagctggggcagagggcggagtacggtgtgcgtttacggacctcttcaaacgaggtaggaaggtcagaagtcaaaaagggaacaa
atgatgtttaaccacacaaaaatgaaaatccaatggttggatatccattccaaatacacaaaggcaacggataagtgatccgggccaggcac
agaaggccatgcacccgtaggattgcactcagagctcccaaatgcataggaatagaagggtgggtgcaggaggctgaggggtggggaa
agggcatgggtgtttcatgaggacagagcttccgtttcatgcaatgaaaagagtttggagacggatggtggtgactggactatacacttacac
acggtagcgatggtacactttgtattatgtatattttaccacgatcttttaaagtgtcaaaggcaaatggccaaatggttccttgtcctatagctgt
agcagccatcggctgttagtgacaaagcccctgagtcaagatgacagcagcccccataactcctaatcggctctcccgcgtggagtcattta
ggagtagtcgcattagagacaagtccaacatctaatcttccaccctggccagggccccagctggcagcgagggtgggagactccgggca
gagcagagggcgctgacattgggcccggcctggcttgggtccctctggcctttccccaggggccctctttccttggggctttcttgggccg
ccactgctcccgctcctctcccccccatcccacccccctcaccccctcgttcttcatatccttctctagtgctccctccactttcatccacccttctgc
aagagtgtgggaccacaaatgagttttcacctggcctggggacacacgtgcccccacaggtgctgagtgactttctaggacagtaatctgct
ttaggctaaaatgggacttgatcttctgttagccctaatcatcaattagcagagccggtgaaggtgcagaacctaccgcctttccaggcctcct
cccacctctgccacctccactctccttcctgggatgtgggggctggcacacgtgtggcccagggcattggtgggattgcactgagctgggt
cattagcgtaatcctggacaagggcagacagggcgagcggagggccagctccggggctcaggcaaggctgggggcttcccccagaca
ccccactcctcctctgctggaccccacttcatagggcacttcgtgttctcaaagggcttccaaatagcatggtggccttggatgcccaggga
agcctcagagttgcttatctccctctagacagaagggaatctcggtcaagagggagaggtcgccctgttcaaggccacccagccagctca
tggcggtaatgggacaaggctggccagccatcccaccctcagaagggacccggtggggcaggtgatctcagaggaggctcacttctgg
gtctcacattcttggatccggttccaggcctcggccctaaatagtctccctgggctttcaagagaaccacatgagaaaggaggattcgggctc
tgagcagtttcaccaccaccccccagtctgcaaatcctgacccgtgggtccacctgccccaaaggcggacgcaggacagtagaaggga
acagagaacacataaacacagagagggccacagcggctcccacagtcaccgccaccttcctggcggggatgggtggggcgtctgagttt
ggttcccagcaaatccctctgagccgcccttgcgggctcgcctcaggagcaggggagcaagaggtgggaggaggaggtctaagtccca
ggcccaattaagagatcaggtagtgtagggtttgggagcttttaaggtgaagaggcccgggctgatcccacaggccagtataaagcgccgt
gaccctcaggtgatgcgccagggccggctgccgtcggggacagggctttccatagccatg

SEQUENCE LISTING

<160> NUMBER OF SEQ ID NOS: 8

<210> SEQ ID NO 1
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gtgggaccac aaatgagttt tcacctggcc tggggacaca cgtgccccca caggtgctga     60
gtgactttct aggacagtaa tctgctttag gctaaaatgg gacttgatct tctgttagcc    120
ctaatcatca attagcagag ccggtgaagg tgcagaacct accgcctttc caggcctcct    180
cccacctctg ccacctccac tctccttcct gggatgtggg ggctggcaca cgtgtggccc    240
agggcattgg tgggattgca ctgagctggg tcattagcgt aatcctggac aagggcagac    300
agggcgagcg gagggccagc tccggggctc aggcaaggct gggggcttcc cccagacacc    360
ccactcctcc tctgctggac ccccacttca tagggcactt cgtgttctca aagggcttcc    420
aaatagcatg gtggccttgg atgcccaggg aagcctcaga gttgcttatc tccctctaga    480
cagaagggga atctcggtca agagggagag gtcgccctgt tcaaggccac ccagccagct    540
catggcggta atgggacaag gctggccagc catcccaccc tcagaaggga cccggtgggg    600
caggtgatct cagaggaggc tcacttctgg gtctcacatt cttggatccg gttccaggcc    660
tcggccctaa atagtctccc tgggctttca agagaaccac atgagaaagg aggattcggg    720
ctctgagcag tttcaccacc cacccccag tctgcaaatc ctgacccgtg ggtccacctg     780
ccccaaaggc ggacgcagga cagtagaagg gaacagagaa cacataaaca cagagagggc    840
cacagcggct cccacagtca ccgccacctt cctggcgggg atgggtgggg cgtctgagtt    900
tggttcccag caaatccctc tgagccgccc ttgcgggctc gcctcaggag caggggagca    960
agaggtggga ggaggaggtc taagtcccag gcccaattaa gagatcaggt agtgtagggt   1020
ttgggagctt ttaaggtgaa gaggcccggg ctgatcccac aggccagtat aaagcgccgt   1080
gaccctcagg tgatgcgcca gggccggctg ccgtcgggga cagggctttc catagccatg   1140
```

<210> SEQ ID NO 2
<211> LENGTH: 1513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
agccatcggc tgttagtgac aaagcccctg agtcaagatg acagcagccc ccataactcc     60
taatcggctc tcccgcgtgg agtcatttag gagtagtcgc attagagaca agtccaacat    120
ctaatcttcc accctggcca gggcccagc tggcagcgag ggtgggagac tccgggcaga    180
gcagagggcg ctgacattgg ggcccggcct ggcttgggtc cctctggcct ttccccaggg    240
gccctctttc cttgggcgtt tcttgggccg ccactgctcc cgctcctctc ccccatccc    300 accccctcac cccctcgttc ttcatatcct tctctagtgc tccctccact ttcatccacc    360
cttctgcaag agtgtgggac cacaaatgag ttttcacctg gcctggggac acacgtgccc    420
ccacaggtgc tgagtgactt tctaggacag taatctgctt taggctaaaa tgggacttga    480
tcttctgtta gccctaatca tcaattagca gagccggtga aggtgcagaa cctaccgcct    540
```

| | |
|---|---|
| ttccaggcct cctcccacct ctgccacctc cactctcctt cctgggatgt ggggctggc | 600 |
| acacgtgtgg cccagggcat tggtgggatt gcactgagct gggtcattag cgtaatcctg | 660 |
| gacaagggca gacagggcga gcggagggcc agctccgggg ctcaggcaag gctgggggct | 720 |
| tcccccagac accccactcc tcctctgctg accccccact tcatagggca cttcgtgttc | 780 |
| tcaaagggct tccaaatagc atggtggcct tggatgccca gggaagcctc agagttgctt | 840 |
| atctccctct agacagaagg ggaatctcgg tcaagaggga gaggtcgccc tgttcaaggc | 900 |
| cacccagcca gctcatggcg gtaatgggac aaggctggcc agccatccca ccctcagaag | 960 |
| ggacccggtg gggcaggtga tctcagagga ggctcacttc tgggtctcac attcttggat | 1020 |
| ccggttccag gcctcggccc taaatagtct ccctgggctt caagagaac cacatgagaa | 1080 |
| aggaggattc gggctctgag cagtttcacc acccaccccc cagtctgcaa atcctgaccc | 1140 |
| gtgggtccac ctgccccaaa ggcggacgca ggacagtaga agggaacaga gaacacataa | 1200 |
| acacagagag ggccacagcg gctcccacag tcaccgccac cttcctggcg gggatgggtg | 1260 |
| gggcgtctga gtttggttcc cagcaaatcc ctctgagccg cccttgcggg ctcgcctcag | 1320 |
| gagcagggga gcaagaggtg ggaggaggag gtctaagtcc caggcccaat taagagatca | 1380 |
| ggtagtgtag ggtttgggag cttttaaggt gaagaggccc gggctgatcc cacaggccag | 1440 |
| tataaagcgc cgtgaccctc aggtgatgcg ccagggccgg ctgccgtcgg ggacagggct | 1500 |
| ttccatagcc atg | 1513 |

<210> SEQ ID NO 3
<211> LENGTH: 1727
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| ggaggctgag gggtggggaa agggcatggg tgtttcatga ggacagagct tccgtttcat | 60 |
| gcaatgaaaa gagtttggag acggatggtg gtgactggac tatacactta cacacggtag | 120 |
| cgatggtaca cttttgtatta tgtatatttt accacgatct ttttaaagtg tcaaaggcaa | 180 |
| atggccaaat ggttccttgt cctatagctg tagcagccat cggctgttag tgacaaagcc | 240 |
| cctgagtcaa gatgacagca gcccccataa ctcctaatcg gctctcccgc gtggagtcat | 300 |
| ttaggagtag tcgcattaga gacaagtcca acatctaatc ttccaccctg gccagggccc | 360 |
| cagctggcag cgagggtggg agactccggg cagagcagag ggcgctgaca ttggggcccg | 420 |
| gcctggcttg ggtccctctg gcctttcccc aggggccctc tttccttggg gctttcttgg | 480 |
| gccgccactg ctcccgctcc tctccccca tccacccc tcaccccctc gttcttcata | 540 |
| tccttctcta gtgctccctc cactttcatc caccttctg caagagtgtg ggaccacaaa | 600 |
| tgagttttca cctggcctgg ggacacacgt gcccccacag gtgctgagtg actttctagg | 660 |
| acagtaatct gctttaggct aaaatgggac ttgatcttct gttagccta atcatcaatt | 720 |
| agcagagccg gtgaaggtgc agaacctacc gcctttccag gcctcctccc acctctgcca | 780 |
| cctccactct ccttcctggg atgtgggggc tggcacacgt gtggcccagg gcattggtgg | 840 |
| gattgcactg agctgggtca ttagcgtaat cctggacaag gcagacagg gcgagcggag | 900 |
| ggccagctcc ggggctcagg caaggctggg ggcttccccc agacaccca ctcctcctct | 960 |
| gctggacccc cacttcatag ggcacttcgt gttctcaaag ggcttccaaa tagcatggtg | 1020 |

```
gccttggatg cccagggaag cctcagagtt gcttatctcc ctctagacag aagggaatc    1080 tcggtcaaga gggagaggtc gccctgttca aggccaccca gccagctcat ggcggtaatg    1140
ggacaaggct ggccagccat cccacccctca gaagggaccc ggtggggcag gtgatctcag    1200
aggaggctca cttctgggtc tcacattctt ggatccggtt ccaggcctcg ccctaaata    1260 gtctccctgg gctttcaaga gaaccacatg agaaggagg attcgggctc tgagcagttt    1320
caccacccac cccccagtct gcaaatcctg acccgtgggt ccacctgccc caaggcgga    1380 cgcaggacag tagaagggaa cagagaacac ataaacacag agagggccac agcggctccc    1440
acagtcaccg ccaccttcct ggcggggatg ggtggggcgc tgagtttgg ttcccagcaa    1500 atccctctga gccgcccttg cgggctcgcc tcaggagcag gggagcaaga ggtgggagga    1560
ggaggtctaa gtcccaggcc caattaagag atcaggtagt gtagggtttg ggagctttta    1620
aggtgaagag gcccgggctg atcccacagg ccagtataaa gcgccgtgac cctcaggtga    1680
tgcgccaggg ccggctgccg tcggggacag ggctttccat agccatg    1727
```

<210> SEQ ID NO 4
<211> LENGTH: 2064
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
cccctacagc agccagggtg agattatgag gctgagctga gaatatcaag actgtaccga    60 gtaggggcc ttggcaagtg tggagagccc ggcagctggg gcagagggcg gagtacggtg    120
tgcgtttacg gacctcttca aacgaggtag gaaggtcaga agtcaaaaag ggaacaaatg    180
atgtttaacc acacaaaaat gaaaatccaa tggttggata tccattccaa atacacaaag    240
gcaacggata agtgatccgg gccaggcaca gaaggccatg cacccgtagg attgcactca    300
gagctcccaa atgcatagga atagaagggt gggtgcagga ggctgagggg tggggaaagg    360
gcatgggtgt tcatgagga cagagcttcc gtttcatgca atgaaaagag tttggagacg    420
gatggtggtg actggactat acacttacac acggtagcga tggtacactt tgtattatgt    480 atatttacc acgatctttt taaagtgtca aaggcaaatg ccaaatggt tccttgtcct    540 atagctgtag cagccatcgg ctgttagtga caaagcccct gagtcaagat gacagcagcc    600
cccataactc ctaatcggct ctcccgcgtg gagtcattta ggagtagtcg cattagagac    660
aagtccaaca tctaatcttc caccctggcc agggcccag ctggcagcga gggtgggaga    720
ctccgggcag agcagagggc gctgacattg gggcccggcc tggcttgggt ccctctggcc    780 ttttccccagg ggccctcttt ccttggggct tcttgggcc gccactgctc ccgctcctct    840 cccccccatcc cacccctca cccctcgtt cttcatatcc ttctctagtg ctccctccac    900
tttcatccac ccttctgcaa gagtgtggga ccacaaatga gttttcacct ggcctgggga    960
cacacgtgcc cccacaggt ctgagtgact ttctaggaca gtaatctgct ttaggctaaa    1020
atgggacttg atcttctgtt agccctaatc atcaattagc agagccggtg aaggtgcaga    1080
acctaccgcc tttccaggcc tcctcccacc tctgccacct ccactctcct tcctgggatg    1140 tggggggctgg cacacgtgtg tgcccaggca ttggtgggat tgcactgagc tgggtcatta    1200
gcgtaatcct ggacaaggc agacaggcg agcggaggc cagctccggg gctcaggcaa    1260
ggctgggggc ttcccccaga caccccactc ctcctctgct ggaccccac ttcatagggc    1320
```

```
acttcgtgtt ctcaaagggc ttccaaatag catggtggcc ttggatgccc agggaagcct    1380
cagagttgct tatctccctc tagacagaag gggaatctcg gtcaagaggg agaggtcgcc    1440
ctgttcaagg ccacccagcc agctcatggc ggtaatggga caaggctggc cagccatccc    1500
accctcagaa gggacccggt ggggcaggtg atctcagagg aggctcactt ctgggtctca    1560
cattcttgga tccggttcca ggcctcggcc ctaaatagtc tccctgggct ttcaagagaa    1620
ccacatgaga aaggaggatt cgggctctga gcagtttcac cacccacccc ccagtctgca    1680
aatcctgacc cgtgggtcca cctgccccaa aggcggacgc aggacagtag aagggaacag    1740
agaacacata aacacagaga gggccacagc ggctcccaca gtcaccgcca ccttcctggc    1800
ggggatgggt ggggcgtctg agtttggttc ccagcaaatc cctctgagcc gcccttgcgg    1860
gctcgcctca ggagcagggg agcaagaggt ggggaggagga ggtctaagtc ccaggcccaa    1920
ttaagagatc aggtagtgta gggtttggga gcttttaagg tgaagaggcc cgggctgatc    1980
ccacaggcca gtataaagcg ccgtgaccct caggtgatgc gccagggccg gctgccgtcg    2040
gggacagggc tttccatagc catg                                          2064

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatttaagct tgcggccgcg ggtacaattc cgcagctttt agag                      44

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgcaagctt gtgggaccac aaatcag                                         27

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tagcggtacc agccatcggc tgttag                                          26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgggtaccg gaggctgagg ggtg                                            24
```

PROMOTERS, EXPRESSION CASSETTES, VECTORS, KITS, AND METHODS FOR THE TREATMENT OF ACHROMATOPSIA AND OTHER DISEASES

RELATED APPLICATIONS

This application claims priority to U.S. Provisional Application 61/824,071, filed on May 16, 2013, the entire contents of which are incorporated by reference in its entirety herein.

SEQUENCE LISTING

The instant application contains a Sequence Listing which has been submitted electronically in ASCII format and is hereby incorporated by reference in its entirety. Said ASCII copy, created on Aug. 12, 2014, is named 119561_00603_SL.txt and is 10,400 bytes in size.

BACKGROUND OF THE INVENTION

Achromatopsia is an autosomal recessive retinal disease characterized by markedly reduced visual acuity, nystagmus, severe photophobia under daylight conditions, and reduced or complete loss of color discrimination (Kohl, S. et al. Achromatopsia. In: Pagon R A, Bird T C, Dolan C R, Stephens K, editors Gene Reviews [Internet]. Seattle: University of Washington; 2010). It may be partial or complete. See Pang, J.-J. et al. (2010). Achromatopsia as a Potential Candidate for Gene Therapy. In *Advances in Experimental Medicine and Biology*, Volume 664, Part 6, 639-646 (2010) (hereinafter Pang et al). Symptoms of achromatopsia include reduced visual acuity, achromatopia (lack of color perception), hemeralopia (reduced visual capacity in bright light accompanied by photoaversion, meaning a dislike or avoidance of bright light), nystagmus (uncontrolled oscillatory movement of the eyes), iris operating abnormalities, and impaired stereovision (inability to perceive three-dimensional aspects of a scene). Electroretinograms reveal that in achromatopsia, the function of retinal rod photoreceptors remains intact, whereas retinal cone photoreceptors are not functional. Mutations in the cone-specific cyclic nucleotide gated channel beta subunit (CNGB3) gene account for about 50% of cases of achromatopsia (Kohl S, et al. Eur J Hum Genet. 2005; 13:302-8). The rod and cone photoreceptors serve functionally different roles in vision. Pang et al. (2010). Cone photoreceptors are primarily responsible for central, fine resolution and color vision while operating in low to very bright light. They are concentrated in the central macula of the retina and comprise nearly 100% of the fovea. Rod photoreceptors are responsible for peripheral, low light, and night vision; they are found primarily outside the macula in the peripheral retina.

Approximately 1 in 30,000 individuals suffers from complete achromatopsia. In complete achromatopsia, there is total color vision loss, central vision loss, and visual acuity of 20/200 or worse. Thus, most individuals with achromatopsia are legally blind. The current standard of care consists of limiting retinal light exposure with tinted contact lenses and providing magnification to boost central vision. However, there is no treatment available that corrects cone function in achromatopsia. Pang et al.

There are various genetic causes of congenital achromatopsia. Mutations in the cyclic nucleotide-gated ion channel beta 3 (CNGB3, also known as ACHM3) gene, are one genetic cause of achromatopsia. Recent studies in dogs suggest some promise for the use of recombinant adeno-associated virus (rAAV)-based gene therapy for the treatment of achromatopsia caused by mutations in the CNGB3 gene. Komaromy et al., Gene therapy rescues cone function in congenital achromatopsia. *Human Molecular Genetics*, 19(13): 2581-2593 (2010) (hereinafter Komaromy et al.). In the canine studies, the rAAV vectors that were used packaged a human CNGB3 (hCNGB3) expression cassette that contained elements including a 2.1 kb cone red opsin promoter (PR2.1) and a human CNGB3 (hCNGB3) cDNA. One limitation of the studies is that the hCNGB3 driven by the PR2.1 promoter is expressed only in red and green cones, whereas endogenous hCNGB3 is expressed in all three types of cones (red, green and blue cones). Another limitation is that the overall size of the expression cassette utilized (5,230 bp) was well beyond the normal packaging capacity (<4.9 kb) of AAV particles; the over-stuffed rAAV particles dramatically impaired the rAAV packaging efficiency, resulting in low yields, a higher empty-to-full particle ratio, and likely a lower infectivity of the vector. Expression cassettes containing a shorter version of the cone red opsin promoter, or a cone arrestin promoter, were much less effective in restoring visual function. The present invention addresses these limitations.

The present invention has the advantage of providing promoters that are capable of promoting hCNGB3 expression in all three types of cones. In addition, the promoters of the invention have the advantage that they are short enough to make the hCNGB3 expression cassette fit well within the normal packaging capacity of rAAV. A promoter that fits within the normal rAAV packaging capacity provides benefits, such as improved yields, a lower empty-to-full particle ratio, and higher infectivity of the vector. The present invention also provides expression cassettes, vectors and kits that utilize these improved promoters, as well as methods for treating achromatopsia by administering the vectors.

The present invention addresses the need for an effective achromatopsia treatment.

SUMMARY OF THE INVENTION

The present invention features, in a first aspect, a nucleic acid comprising a portion of the cone cell specific promoter PR 2.1.

In one embodiment, the nucleic acid comprises the sequence SEQ ID NO: 4. In another embodiment, PR2.1 is truncated at the 5' or the 3' end. In a related embodiment, the truncation is between about 100 base pairs to 1,500 base pairs. In a further related embodiment, the truncation is about 300 base pairs at the 5' end. In another further embodiment, the truncation is about 500 base pairs at the 5' end. In another embodiment, the truncation is about 1,1000 base pairs at the 5' end. In another further embodiment, the truncation is about 300 base pairs at the 3' end. In another embodiment, the truncation is about 500 base pairs at the 3' end. In another further embodiment, the truncation is about 1,1000 base pairs at the 3' end.

In one embodiment, the nucleic acid of the above aspects and embodiments comprises SEQ ID NO:3. In one embodiment, the nucleic acid of the above aspects and embodiments comprises SEQ ID NO:2. In one embodiment, the nucleic acid of the above aspects and embodiments comprises SEQ ID NO:1.

In another aspect, the invention features a nucleic acid comprising the nucleotide sequence of SEQ ID NO:1. In another aspect, the invention features a nucleic acid comprising the nucleotide sequence of SEQ ID NO:2. In another aspect, the invention features a nucleic acid comprising the nucleotide sequence of SEQ ID NO:3.

In another further embodiment, the invention features a nucleic acid comprising a nucleotide sequence which is at least 85% identical to the nucleotide sequence of SEQ ID NO:1.

In one embodiment of the above aspects, the promoter is capable of promoting CNGB3 expression in S-cone cells, M-cone cells, and L-cone cells. In another embodiment of the above aspects, the promoter is capable of promoting CNGA3 expression in S-cone cells, M-cone cells, and L-cone cells. In yet another embodiment of the above aspects, the promoter is capable of promoting GNAT2 expression in S-cone cells, M-cone cells, and L-cone cells.

In another embodiment, the invention features a recombinant adeno-associated (rAAV) expression vector comprising a target nucleic acid sequence operably linked to the nucleic acid of any one of the above aspects and embodiments. In a related embodiment, the rAAV is serotype 1. In a related embodiments, the rAAV is serotype 2. In another related embodiment, the rAAV is serotype 5. In still another related embodiment, the rAAV is comprised within an AAV virion.

In one embodiment, the target nucleic acid sequence encodes a cyclic nucleotide-gated channel subunit B (CNGB3) polypeptide. In a related embodiment, the CNGB3 is mouse CNGB3. In another related embodiment, the CNGB3 is rat CNGB3. In still another related embodiment, the CNGB3 is human CNGB3.

In one embodiment, the target nucleic acid sequence encodes a cyclic nucleotide-gated channel subunit A (CNGA3) polypeptide. In a related embodiment, the CNGA3 is mouse CNGA3. In another related embodiment, the CNGA3 is rat CNGA3. In still another related embodiment, the CNGA3 is human CNGA3.

In one embodiment, the target nucleic acid sequence encodes a Guanine nucleotide-binding protein G(t) subunit alpha-2 (GNAT-2) polypeptide. In a related embodiment, the GNAT-2 is mouse GNAT-2. In another related embodiment, the GNAT-2 is rat GNAT-2. In still another related embodiment, the GNAT-2 is human In another embodiment, the invention features a mammalian cell comprising the expression vector of any one of the above aspects and embodiments.

In still another embodiment, the invention features a transgene expression cassette comprising the nucleic acid of any of the above aspects or embodiments, a nucleic acid selected from the group consisting of a CNGB3 nucleic acid, a CNGA3 nucleic acid, and a GNAT2 nucleic acid, and minimal regulatory elements. In one embodiment, the invention features a nucleic acid vector comprising the expression cassette of any one of the above aspects or embodiments. In a related embodiment, the vector is an adeno-associated viral (AAV) vector.

In another embodiment, the invention features a kit comprising the expression vector of any one of the above aspects or embodiments and instructions for use.

The invention also features in another embodiment, a method of treating an eye disease comprising administering to a subject in need thereof the expression vector of any one of the above aspects or embodiments, thereby treating the subject.

The invention also features in another embodiment, a method of promoting CNGA3 or CNGB3 expression in the cone cells of a subject comprising administering to the subject the expression vector of any one of the above aspects or embodiments, thereby promoting CNGA3 or CNGB3 expression.

In one embodiment, the eye disease is associated with a genetic mutation, substitution, or deletion that affects retinal cone cells. In another embodiment, the eye disease affects the retinal pigment epithelium. In another related embodiment, the eye disease is achromatopsia.

In another embodiment, the expression vector is capable of promoting CNGB3 expression in S-cone cells, M-cone cells, and L-cone cells. In another further embodiment, the expression vector is capable of promoting CNGA3 expression in S-cone cells, M-cone cells, and L-cone cells. In still another further embodiment, the expression vector is capable of promoting GNAT-2 expression in S-cone cells, M-cone cells, and L-cone cells.

In further embodiments, the vector is administered subretinally.

BRIEF DESCRIPTION OF THE DRAWINGS

FIG. 4A sets forth SEQ ID NO 1. FIG. 4B sets forth SEQ ID NO 2. FIG. 4C sets forth SEQ ID NO 3. FIG. 4D sets forth SEQ ID NO 4.

DETAILED DESCRIPTION OF THE INVENTION

I. Overview and Definitions

Figure 1:
FIG. 1: Schematic drawing of the truncated human red/green opsin promoter.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

A "subject" or "patient" to be treated by the method of the invention can mean either a human or non-human animal. A "nonhuman animal" includes any vertebrate or invertebrate organism.

"Achromatopsia" is a color vision disorder. Symptoms of achromatopsia include achromatopia (lack of color perception), amblyopia (reduced visual acuity), hemeralopia (reduced visual capacity in bright light accompanied by photoaversion, meaning a dislike or avoidance of bright light), nystagmus (uncontrolled oscillatory movement of the eyes), iris operating abnormalities, and impaired stereovision (inability to perceive three-dimensional aspects of a scene). As used herein, the term "achromatopsia" refers to a form of achromatopsia caused by genetic mutations, substitutions, or deletions.

"Treating" a disease (such as, for example, achromatopsia) means alleviating, preventing, or delaying the occurrence of at least one sign or symptom of the disease.

The asymmetric ends of DNA and RNA strands are called the 5' (five prime) and 3' (three prime) ends, with the 5' end having a terminal phosphate group and the 3' end a terminal hydroxyl group. The five prime (5') end has the fifth carbon in the sugar-ring of the deoxyribose or ribose at its terminus. Nucleic acids are synthesized in vivo in the 5'- to 3'-direction, because the polymerase used to assemble new strands attaches each new nucleotide to the 3'-hydroxyl (—OH) group via a phosphodiester bond.

A "promoter" is a region of DNA that facilitates the transcription of a particular gene. As part of the process of transcription, the enzyme that synthesizes RNA, known as RNA polymerase, attaches to the DNA near a gene. Promoters contain specific DNA sequences and response elements that provide an initial binding site for RNA polymerase and for transcription factors that recruit RNA polymerase.

The retina contains three kinds of photoreceptors: rod cells, cone cells, and photoreceptive ganglion cells. Cone cells are of three types: S-cone cells, M-cone cells, and L-cone cells. S-cone cells respond most strongly to short wavelength light (peak near 420-440 nm) and are also known as blue cones. M-cone cells respond most strongly to medium wavelength light (peak near 534-545 nm) and are also known as green cones. L-cone cells respond most strongly to light of long wavelengths (peak near 564-580 nm) and are also known as red cones. The difference in the signals received from the three cone types allows the brain to perceive all possible colors.

A "transgene expression cassette" or "expression cassette" comprises the gene sequences that a nucleic acid vector is to deliver to target cells. These sequences include the gene of interest (e.g., a CNGB3 or CNGA3 nucleic acid), one or more promoters, and minimal regulatory elements.

"Minimal regulatory elements" are regulatory elements that are necessary for effective expression of a gene in a target cell and thus should be included in a transgene expression cassette. Such sequences could include, for example, promoter or enhancer sequences, a polylinker sequence facilitating the insertion of a DNA fragment within a plasmid vector, and sequences responsible for intron splicing and polyadenlyation of mRNA transcripts. In a recent example of a gene therapy treatment for achromatopsia, the expression cassette included the minimal regulatory elements of a polyadenylation site, splicing signal sequences, and AAV inverted terminal repeats. See, e.g., Komaromy et al.

A "nucleic acid" or "nucleic acid molecule" is a molecule composed of chains of monomeric nucleotides, such as, for example, DNA molecules (e.g., cDNA or genomic DNA). A nucleic acid may encode, for example, a promoter, the CNGB3 or CNGA3 gene or portion thereof, or regulatory elements. A nucleic acid molecule can be single-stranded or double-stranded. A "CNGB3 nucleic acid" refers to a nucleic acid that comprises the CNGB3 gene or a portion thereof, or a functional variant of the CNGB3 gene or a portion thereof. Similarly, a "CNGA3 nucleic acid" refers to a nucleic acid that comprises the CNGA3 gene or a portion thereof, or a functional variant of the CNGA3 gene or a portion thereof, and a "GNAT2 nucleic acid" refers to a nucleic acid that comprises the GNAT2 gene or a portion thereof, or a functional variant of the GNAT2 gene or a portion thereof. A functional variant of a gene includes a variant of the gene with minor variations such as, for example, silent mutations, single nucleotide polymorphisms, missense mutations, and other mutations or deletions that do not significantly alter gene function.

An "isolated" nucleic acid molecule (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

II. Methods of the Invention

The present invention provides promoters, expression cassettes, vectors, kits, and methods that can be used in the treatment of genetic diseases that affect the cone cells of the retina. Genetic diseases that affect the cone cells of the retina include achromatopsia; Leber congenital amaurosis; cone-rod dystrophy; retinitis pigmentosa, including X-linked retinitis pigmentosa; maculopathies; and age-related macular degeneration. In preferred embodiments, the disease is achromatopsia.

Achromatopsia is a color vision disorder. Autosomal recessive mutations or other types of sequence alterations in three genes are the predominant cause of congenital achromatopsia. See Pang, J.-J. et al. (2010). Achromatopsia as a Potential Candidate for Gene Therapy. In Advances in Experimental Medicine and Biology, Volume 664, Part 6, 639-646 (2010). Achromatopsia has been associated with mutations in either the alpha or beta subunits of cyclic nucleotide gated channels (CNGs), which are respectively known as CNGA3 and CNGB3. Mutations in the CNGA3 gene that were associated with achromatopsia are reported in Patel K A, et al. Transmembrane 51 mutations in CNGA3 from achromatopsia 2 patients cause loss of function and impaired cellular trafficking of the cone CNG channel Invest. Ophthalmol. Vis. Sci. 46 (7): 2282-90. (2005)., Johnson S, et al. Achromatopsia caused by novel mutations in both CNGA3 and CNGB3. J. Med. Genet. 41 (2): e20. (2004)., Wissinger B, et al. CNGA3 mutations in hereditary cone photoreceptor disorders. Am. J. Hum. Genet. 69 (4): 722-37. (2001)., and Kohl S, et al. Total colourblindness is caused by mutations in the gene encoding the alpha-subunit of the cone photoreceptor cGMP-gated cation channel Nat. Genet. 19 (3): 257-9. (1998). Mutations in CNGB3 gene that were associated with achromatopsia are reported in Johnson S, et al. Achromatopsia caused by novel mutations in both CNGA3 and CNGB3. J. Med. Genet. 41 (2): e20. (2004)., Peng C, et al. Achromatopsia-associated mutation in the human cone photoreceptor cyclic nucleotide-gated channel CNGB3 subunit alters the ligand sensitivity and pore properties of heteromeric channels. J. Biol. Chem. 278 (36): 34533-40 (2003)., Bright S R, et al. Disease-associated mutations in CNGB3 produce gain of function alterations in cone cyclic nucleotide-gated channels. Mol. Vis. 11: 1141-50 (2005)., Kohl S, et al. CNGB3 mutations account for 50% of all cases with autosomal recessive achromatopsia. Eur. J. Hum. Genet. 13 (3): 302-8 (2005)., Rojas C V, et al. A frameshift insertion in the cone cyclic nucleotide gated cation channel causes complete achromatopsia in a consanguineous family from a rural isolate. Eur. J. Hum. Genet. 10 (10): 638-42 (2002)., Kohl S, et al. Mutations in the CNGB3 gene encoding the beta-subunit of the cone photoreceptor cGMP-gated channel are responsible for achromatopsia (ACHM3) linked to chromosome 8q21. Hum. Mol. Genet. 9 (14): 2107-16 (2000)., Sundin O H, et al., Genetic basis of total colourblindness among the Pingelapese islanders. Nat. Genet. 25 (3): 289-93 (2000). Sequence alterations in the gene for cone cell transducin, known as GNAT2, can also cause achromatopsia. See Kohl S, et al., Mutations in the cone photoreceptor G-protein alpha-subunit gene GNAT2 in patients with achromatopsia. Kokl S, et al. Mutations in the cone photoreceptor G-protein alpha-subunit gene GNAT2 in patients with achromatopsia. Am J Hum Genet 71 (2): 422-425 (2002) (hereinafter Kohl et al.). The severity of mutations in these proteins correlates with the severity of the achromatopsia phenotype. en.wikipedia.org/wiki/Achromatopsia. Mutations in CNGB3 account for about 50% of cases of achromatopsia. Kohl et al. Mutations in CNGA3 account for about 23% of cases, and mutations in GNAT2 account for about 2% of cases.

The "CNGB3 gene" is the gene that encodes the cyclic nucleotide-gated channel beta 3 (CNGB3). The "CNGA3 gene" is the gene that encodes the cyclic nucleotide-gated channel alpha 3 (CNGA3). The CNGB3 and CNGA3 genes are expressed in cone cells of the retina. Native retinal cyclic nucleotide gated channels (CNGs) are critically involved in phototransduction. CNGs are cation channels that consist of two alpha and two beta subunits. In the dark, cones have a relatively high concentration of cyclic guanosine 3'-5' monophosphate (cGMP), which causes the CNGs to open, resulting in depolarization and continuous glutamate release. Light exposure activates a signal transduction pathway that breaks down cGMP. The reduction in cGMP concentration causes the CNGs to close, preventing the influx of positive ions, hyperpolarizing the cell, and stopping the release of glutamate. Mutations in either the CNGB3 or CNGA3 genes can cause defects in cone photoreceptor function resulting in achromatopsia. Mutations in the CNGB3 gene have been associated with other diseases in addition to achromatopsia, including progressive cone dystrophy and juvenile macular degeneration.

The GNAT2 gene encodes the alpha-2 subunit of guanine nucleotide binding protein, which is also known as the cone-specific alpha transducin. Guanine nucleotide-binding proteins (G proteins) consist of alpha, beta, and gamma subunits. In photoreceptors, G proteins are critical in the amplification and transduction of visual signals. Various types of sequence alterations in GNAT2 can cause human achromatopsia: nonsense mutations, small deletion and/or insertion mutations, frameshift mutations, and large intragenic deletions. Pang et al.

Currently, there is no effective treatment for achromatopsia. Animal studies suggest that it is possible to use gene therapy to treat achromatopsia and other diseases of the retina. For recessive gene defects, the goal is to deliver a wild-type copy of a defective gene to the affected retinal cell type. The ability to deliver genes to some subsets of cone cells was demonstrated, for example, in Mauck, M. C. et al., Longitudinal evaluation of expression of virally delivered transgenes in gerbil cone photoreceptors. *Visual Neuroscience* 25(3): 273-282 (2008). The authors showed that a recombinant AAV vector could be used to achieve long-term expression of a reporter gene encoding green fluorescent protein in specific types of gerbil cone cells. The authors further demonstrated that a human long-wavelength opsin gene could be delivered to specific gerbil cones, resulting in cone responses to long-wavelength light.

Other studies demonstrated that gene therapy with recombinant AAV vectors could be used to convert dichromat monkeys into trichromats by introducing a human L-opsin gene into the squirrel monkey retina. Mancuso, K., et al. Gene therapy for red-green colour blindness in adult primates. *Nature* 461: 784-787 (2009). Electroretinograms verified that the introduced photopigment was functional, and the monkeys showed improved color vision in a behavioral test.

There are several animal models of achromatopsia for which gene therapy experiments have demonstrated the ability to restore cone function. See Pang et al. First, the Gnat2$^{cpfl3}$ mouse has a recessive mutation in the cone-specific alpha transducin gene, resulting in poor visual acuity and little or no cone-specific ERT response. Treatment of homozygous Gnat2$^{cpfl3}$ mice with a single subretinal injection of an AAV serotype 5 vector carrying wild type mouse GNAT2 cDNA and a human red cone opsin promoter restored cone-specific ERG responses and visual acuity. Alexander et al. Restoration of cone vision in a mouse model of achromatopsia. *Nat Med* 13:685-687 (2007) (hereinafter Alexander et al.). Second, the cpfl5 (Cone Photoreceptor Function Loss 5) mouse has an autosomal recessive missense mutation in the CNGA3 gene with no cone-specific ERG response. Treatment of cpfl5 mice with subretinal injection of an AAV vector carrying the wild type mouse CNGA3 gene and a human blue cone promoter (HB570) resulted in restoration of cone-specific ERG responses. Pang et al. Third, there is an Alaskan Malmute dog that has a naturally occurring CNGB3 mutation causing loss of daytime vision and absence of retinal cone function. In this type of dog, subretinal injection of an AAV5 vector containing human CNGB3 cDNA and a human red cone opsin promoter restored cone-specific ERG responses. See, e.g., Komaromy et al.

The prior methods for treatment of achromatopsia using gene therapy were limited by the fact that the promoters used caused expression of transgenes only in certain types of cone cell photoreceptors. The promoters of the present invention can drive gene expression in all three types of cone cells that are present in humans (S-cone cells, M-cone cells, and L-cone cells).

Another limitation of the studies performed by Komaromy et al. was that the overall size of the expression cassette utilized (5,230 bp) was well beyond the normal packaging capacity (<4.9 kb) of AAV particles; the overstuffed rAAV particles dramatically impaired the rAAV packaging efficiency, resulting in low yields, a higher empty-to-full particle ratio, and likely a lower infectivity of the vector. Expression cassettes containing a shorter version of the cone red opsin promoter, or a cone arrestin promoter, were much less effective in restoring visual function. The promoters of the present invention have the advantage that due to their shortened length, they make the hCNGB3 expression cassette efficiently package in an AAV particle. A promoter that fits within the normal rAAV packaging capacity provides benefits, such as improved yields, a lower empty-to-full particle ratio, higher infectivity of the vector, and ultimately, higher efficacy for treatment of the desired condition.

III. Promoters, Expression Cassettes, Nucleic Acids, and Vectors of the Invention The promoters, CNGB3 nucleic acids, regulatory elements, and expression cassettes, and vectors of the invention may be produced using methods known in the art. The methods described below are provided as non-limiting examples of such methods.

Promoters

The present invention provides isolated and/or truncated promoters. In some aspects, these promoters include a segment of the PR 2.1 promoter. In one embodiment, the promoter is a truncated PR2.1 promoter.

In some embodiments of the promoters of the invention, the promoter is capable of promoting expression of a transgene in S-cone, M-cone, and L-cone cells. A "transgene" refers to a segment of DNA containing a gene sequence that has been isolated from one organism and is introduced into a different organism. For example, to treat an individual who has achromatopsia caused by a mutation of the human CNGB3 gene, a wild-type (i.e., non-mutated, or functional variant) human CNGB3 gene may be administered using an appropriate vector. The wild-type gene is referred to as a "transgene." In preferred embodiments, the transgene is a wild-type version of a gene that encodes a protein that is normally expressed in cone cells of the retina. In one such embodiment, the transgene is derived from a human gene. In a first specific embodiment, the promoter is capable of promoting expression of a CNGB3 nucleic acid in S-cone, M-cone, and L-cone cells. In a second specific embodiment, the promoter is capable of promoting expression of a CNGA3 nucleic acid in S-cone, M-cone, and L-cone cells. In a third specific embodiment, the promoter is capable of promoting expression of a GNAT2 nucleic acid in S-cone, M-cone, and L-cone cells. In these three specific embodiments, the CNGB3, CNGA3, or GNAT2 is preferably human CNGB3, CNGA3, or GNAT2.

In another aspect, the present invention provides promoters that are shortened versions of the PR2.1 promoter. Such promoters have the advantage that they fit better within the packaging capacity of AAV particles and therefore provide advantages such as, for example, improved yields, a lower empty-to-full particle ratio, and higher infectivity of the vector. In some embodiments, these promoters are created by truncating the 5'-end of PR2.1 or the 3'-end of PR 2.1. In some such embodiments, the lengths of the truncations are selected from the group consisting of approximately 300 bp, 500 bp, and 1,100 bp (see, e.g., PR1.7, PR1.5, and PR1.1, respectively).

Expression Cassettes

In another aspect, the present invention provides a transgene expression cassette that includes (a) a promoter of the invention; (b) a nucleic acid selected from the group consisting of a CNGB3 nucleic acid, a CNGA3 nucleic acid, and a GNAT2 nucleic acid; and (c) minimal regulatory elements. A promoter of the invention includes the promoters discussed supra.

A "CNGB3 nucleic acid" refers to a nucleic acid that comprises the CNGB3 gene or a portion thereof, or a functional variant of the CNGB3 gene or a portion thereof. Similarly, a "CNGA3 nucleic acid" refers to a nucleic acid that comprises the CNGA3 gene or a portion thereof, or a functional variant of the CNGA3 gene or a portion thereof, and a "GNAT2 nucleic acid" refers to a nucleic acid that comprises the GNAT2 gene or a portion thereof, or a functional variant of the GNAT2 gene or a portion thereof. A functional variant of a gene includes a variant of the gene with minor variations such as, for example, silent mutations, single nucleotide polymorphisms, missense mutations, and other mutations or deletions that do not significantly alter gene function.

In certain embodiments, the nucleic acid is a human nucleic acid (i.e., a nucleic acid that is derived from a human CNGB3, CNGA3, or GNAT2 gene). In other embodiments, the nucleic acid is a non-human nucleic acid (i.e., a nucleic acid that is derived from a non-human CNGB3, CNGA3, or GNAT2 gene).

"Minimal regulatory elements" are regulatory elements that are necessary for effective expression of a gene in a target cell. Such regulatory elements could include, for example, promoter or enhancer sequences, a polylinker sequence facilitating the insertion of a DNA fragment within a plasmid vector, and sequences responsible for intron splicing and polyadenlyation of mRNA transcripts. In a recent example of a gene therapy treatment for achromatopsia, the expression cassette included the minimal regulatory elements of a polyadenylation site, splicing signal sequences, and AAV inverted terminal repeats. See, e.g., Komaromy et al. The expression cassettes of the invention may also optionally include additional regulatory elements that are not necessary for effective incorporation of a gene into a target cell.

Vectors

The present invention also provides vectors that include any one of the expression cassettes discussed in the preceding section. In some embodiments, the vector is an oligonucleotide that comprises the sequences of the expression cassette. In specific embodiments, delivery of the oligonucleotide may be accomplished by in vivo electroporation (see, e.g., Chalberg, T W, et al. phiC31 integrase confers genomic integration and long-term transgene expression in rat retina. *Investigative Ophthalmology & Visual Science*, 46, 2140-2146 (2005) (hereinafter Chalberg et al., 2005)) or electron avalanche transfection (see, e.g., Chalberg, T W, et al. Gene transfer to rabbit retina with electron avalanche transfection. *Investigative Ophthalmology & Visual Science*, 47, 4083-4090 (2006) (hereinafter Chalberg et al., 2006)). In further embodiments, the vector is a DNA-compacting peptide (see, e.g., Farjo, R, et al. Efficient non-viral ocular gene transfer with compacted DNA nanoparticles. *PLoS ONE*, 1, e38 (2006) (hereinafter Farjo et al., 2006), where CK30, a peptide containing a cystein residue coupled to polyethylene glycol followed by 30 lysines, was used for gene transfer to photoreceptors), a peptide with cell penetrating properties (see Johnson, L N, et al., Cell-penetrating peptide for enhanced delivery of nucleic acids and drugs to ocular tissues including retina and cornea. *Molecular Therapy*, 16(1), 107-114 (2007) (hereinafter Johnson et al., 2007), Barnett, E M, et al. Selective cell uptake of modified Tat peptide-fluorophore conjugates in rat retina in ex vivo and in vivo models. *Investigative Ophthalmology & Visual Science*, 47, 2589-2595 (2006) (hereinafter Barnett et al., 2006), Cashman, S M, et al. Evidence of protein transduction but not intercellular transport by proteins fused to HIV tat in retinal cell culture and in vivo. *Molecular Therapy*, 8, 130-142 (2003) (hereinafter Cashman et al., 2003), Schorderet, D F, et al. D-TAT transporter as an ocular peptide delivery system. *Clinical and Experimental Ophthalmology*, 33, 628-635 (2005)(hereinafter Schorderet et al., 2005), Kretz, A, et al. HSV-1 VP22 augments adenoviral gene transfer to CNS neurons in the retina and striatum in vivo. *Molecular Therapy*, 7, 659-669 (2003) (hereinafter Kretz et al. 2003) for examples of peptide delivery to ocular cells), or a DNA-encapsulating lipoplex, polyplex, liposome, or immunoliposome (see e.g., Zhang, Y, et al. Organ-specific gene expression in the rhesus monkey eye following intravenous nonviral gene transfer. *Molecular Vision*, 9, 465-472 (2003) (hereinafter Zhang et al. 2003), Zhu, C, et al. Widespread expression of an exogenous gene in the eye after intravenous administration. *Investigative Ophthalmology & Visual Science*, 43, 3075-3080 (2002) (hereinafter Zhu et al. 2002), Zhu, C., et al. Organ-specific expression of the lacZ gene controlled by the opsin promoter after intravenous gene administration in adult mice. *Journal of Gene Medicine*, 6, 906-912. (2004) (hereinafter Zhu et al. 2004)).

In preferred embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). See e.g., Howarth. In the most preferred embodiments, the vector is an adeno-associated viral (AAV) vector.

Multiple serotypes of adeno-associated virus (AAV), including 12 human serotypes (AAV1, AAV2, AAV3, AAV4, AAV5, AAV6, AAV7, AAV8, AAV9, AAV10, AAV11, and AAV12) and more than 100 serotypes from nonhuman primates have now been identified. Howarth J L et al., Using viral vectors as gene transfer tools. *Cell Biol Toxicol* 26:1-10 (2010) (hereinafter Howarth et al.). In embodiments of the present invention wherein the vector is an AAV vector, the serotype of the inverted terminal repeats (ITRs) of the AAV vector may be selected from any known human or nonhuman AAV serotype. In preferred embodiments, the serotype of the AAV ITRs of the AAV vector is selected from the group consisting of AAV1, AAV2, AAV3, AAV4, AAV5, AAV6, AAV7, AAV8, AAV9, AAV10, AAV11, and AAV12. Moreover, in embodiments of the present invention wherein the vector is an AAV vector, the serotype of the capsid sequence of the AAV vector may be selected from any known human or animal AAV serotype. In some embodiments, the serotype of the capsid sequence of the AAV vector is selected from the group consisting of AAV1, AAV2, AAV3, AAV4, AAV5, AAV6, AAV7, AAV8, AAV9, AAV10, AAV11, and AAV12. In preferred embodiments, the serotype of the capsid sequence is AAV5. In some embodiments wherein the vector is an AAV vector, a pseudotyping approach is employed, wherein the genome of one ITR serotype is packaged into a different serotype capsid. See e.g., Zolutuhkin S. et al. Production and purification of serotype 1, 2, and 5 recombinant adeno-associated viral vectors. *Methods* 28(2): 158-67 (2002). In preferred embodiments, the serotype of the AAV ITRs of the AAV vector and the serotype of the capsid sequence of the AAV vector are independently selected from the group consisting of AAV1, AAV2, AAV3, AAV4, AAV5, AAV6, AAV7, AAV8, AAV9, AAV10, AAV11, and AAV12.

In some embodiments of the present invention wherein the vector is a rAAV vector, a mutant capsid sequence is employed. Mutant capsid sequences, as well as other techniques such as rational mutagenesis, engineering of targeting peptides, generation of chimeric particles, library and directed evolution approaches, and immune evasion modifications, may be employed in the present invention to optimize AAV vectors, for purposes such as achieving immune evasion and enhanced therapeutic output. See e.g., Mitchell A. M. et al. AAV's anatomy: Roadmap for optimizing vectors for translational success. *Curr Gene Ther.* 10(5): 319-340.

Making the Nucleic Acids of the Invention

A nucleic acid molecule (including, for example, a promoter, CNGB3 nucleic acid, CNGA3 nucleic acid, a GNAT2 nucleic acid, or a regulatory element) of the present invention can be isolated using standard molecular biology techniques. Using all or a portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques.

Furthermore, oligonucleotides corresponding to nucleotide sequences of interest can also be chemically synthesized using standard techniques. Numerous methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373, 071, incorporated by reference herein). Automated methods for designing synthetic oligonucleotides are available. See e.g., Hoover, D. M. & Lubowski, J. *Nucleic Acids Research*, 30(10): e43 (2002).

Many embodiments of the invention involve a CNGB3 nucleic acid, a CNGA3 nucleic acid, or a GNAT2 nucleic acid. Some aspects and embodiments of the invention involve other nucleic acids, such as isolated promoters or regulatory elements. A nucleic acid may be, for example, a cDNA or a chemically synthesized nucleic acid. A cDNA can be obtained, for example, by amplification using the polymerase chain reaction (PCR) or by screening an appropriate cDNA library. Alternatively, a nucleic acid may be chemically synthesized.

IV. Methods and Kits of the Invention

Methods of Treatment

The invention provides methods for treating a disease associated with a genetic mutation, substitution, or deletion that affects retinal cone cells, wherein the methods comprise administering to a subject in need of such treatment a vector that includes one of the promoters of the invention, thereby treating the subject. In a preferred embodiment, the disease is achromatopsia. Other diseases associated with a genetic mutation, substitution, or deletion that affects retinal cone cells include achromatopsia, Leber congenital amaurosis, cone-rod dystrophy, maculopathies, age-related macular degeneration and retinitis pigmentosa, including X-linked retinitis pigmentosa.

The invention further provides methods for treating achromatopsia comprising administering any of the vectors of the invention to a subject in need of such treatment, thereby treating the subject.

A "subject" to be treated by the methods of the invention can mean either a human or non-human animal. A "nonhuman animal" includes any vertebrate or invertebrate organism. In some embodiments, the nonhuman animal is an animal model of retinal disease, or of achromatopsia in particular. See e.g., Pang et al., Alexander et al., Komaromy et al. Various large animal models are available for the study of AAV-mediated gene-based therapies in the retina. Stieger K. et al. AAV-mediated gene therapy for retinal disorders inlarge animal models. ILAR J. 50(2): 206-224 (2009). The promoters of the invention are described supra. "Treating" a disease (such as, for example, achromatopsia) means alleviating, preventing, or delaying the occurrence of at least one sign or symptom of the disease. A "sign" of a disease is a manifestation of the disease that can be observed by others or measured by objective methods, such as, e.g., electroretinography or behavioral testing. A "symptom" of a disease is a characteristic of the disease that is subjectively perceived by the subject.

In either of these two methods of treatment, the vector can be any type of vector known in the art. In some embodiments, the vector is a non-viral vector, such as a naked DNA plasmid, an oligonucleotide (such as, e.g., an antisense oligonucleotide, a small molecule RNA (siRNA), a double stranded oligodeoxynucleotide, or a single stranded DNA oligonucleotide). In specific embodiments involving oligonucleotide vectors, delivery may be accomplished by in vivo electroporation (see e.g., Chalberg et al., 2005) or electron avalanche transfection (see e.g., Chalberg et al. 2006). In further embodiments, the vector is a dendrimer/DNA complex that may optionally be encapsulated in a water soluble polymer, a DNA-compacting peptide (see e.g., Farjo et al. 2006, where CK30, a peptide containing a cystein residue coupled to poly ethylene glycol followed by 30 lysines, was used for gene transfer to photoreceptors), a peptide with cell penetrating properties (see Johnson et al. 2007; Barnett et al., 2006; Cashman et al., 2003; Schorder et al., 2005; Kretz et al. 2003 for examples of peptide delivery to ocular cells), or a DNA-encapsulating lipoplex, polyplex, liposome, or immunoliposome (see e.g., Zhang et al. 2003; Zhu et al. 2002; Zhu et al. 2004). In many additional embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). See e.g., Howarth. In preferred embodiments, the vector is an adeno-associated viral (AAV) vector.

In the methods of treatment of the present invention, administering of a vector can be accomplished by any means known in the art. In preferred embodiments, the administration is by subretinal injection. In certain embodiments, the subretinal injection is delivered preferentially to one or more regions where cone density is particularly high (such as e.g., the tapetal zone superior to the optic disc). In other embodiments, the administration is by intraocular injection, intravitreal injection, or intravenous injection. Administration of a vector to the retina may be unilateral or bilateral and may be accomplished with or without the use of general anesthesia.

In the methods of treatment of the present invention, the volume of vector delivered may be determined based on the characteristics of the subject receiving the treatment, such as the age of the subject and the volume of the area to which the vector is to be delivered. It is known that eye size and the volume of the subretinal space differ among individuals and may change with the age of the subject. In embodiments wherein the vector is administered subretinally, vector volumes may be chosen with the aim of covering all or a certain percentage of the subretinal space, or so that a particular number of vector genomes is delivered.

In the methods of treatment of the present invention, the concentration of vector that is administered may differ depending on production method and may be chosen or optimized based on concentrations determined to be therapeutically effective for the particular route of administration. In some embodiments, the concentration in vector genomes per milliliter (vg/ml) is selected from the group consisting of about $10^8$ vg/ml, about $10^9$ vg/ml, about $10^{10}$ vg/ml, about $10^{11}$ vg/ml, about $10^{12}$ vg/ml, about $10^{13}$ vg/ml, and about $10^{14}$ vg/ml. In preferred embodiments, the concentration is in the range of $10^{10}$ vg/ml-$10^{13}$ vg/ml, delivered by subretinal injection or intravitreal injection in a volume of about 0.1 mL, about 0.2 mL, about 0.4 mL, about 0.6 mL, about 0.8 mL, and about 1.0 mL Kits The present invention also provides kits. In one aspect, a kit of the invention comprises a vector that comprises (a) any one of the promoters of the invention and (b) instructions for use thereof. In another aspect, a kit of the invention comprises (a) any one of the vectors of the invention, and (b) instructions for use thereof. The promoters and vectors of the invention are described supra. In some embodiments, a vector of the invention may be any type of vector known in the art, including a non-viral or viral vector, as described supra. In preferred embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). In the most preferred embodiments, the vector is an adeno-associated viral (AAV) vector.

The instructions provided with the kit may describe how the promoter can be incorporated into a vector or how the vector can be administered for therapeutic purposes, e.g., for treating a disease associated with a genetic mutation, substitution, or deletion that affects retinal cone cells. In some embodiments wherein the kit is to be used for therapeutic purposes, the instructions include details regarding recommended dosages and routes of administration.

Methods of Making Recombinant Adeno-Associated Viral Vectors (AAV Vectors)

The present invention also provides methods of making a recombinant adeno-associated viral (rAAV) vector comprising inserting into an adeno-associated viral vector any one of the promoters of the invention (described supra) and a nucleic acid selected from the group consisting of a CNGB3 nucleic acid, a CNGA3 nucleic acid, and a GNAT2 nucleic acid (also described supra). In some embodiments, the nucleic acid is a human nucleic acid, i.e., a nucleic acid derived from a human CNGB3, CNGA or GNAT gene, or a functional variant thereof. In alternative embodiments, the nucleic acid is a nucleic acid derived from a non-human gene.

In the methods of making an rAAV vector that are provided by the invention, the serotype of the capsid sequence and the serotype of the ITRs of said AAV vector are independently selected from the group consisting of AAV1, AAV2, AAV3, AAV4, AAV5, AAV6, AAV7, AAV8, AAV9, AAV10, AAV11, and AAV12. Thus, the invention encompasses vectors that use a pseudotyping approach, wherein the genome of one ITR serotype is packaged into a different serotype capsid. See e.g., Daya S, and Berns, K. I., Gene therapy using adeno-associated virus vectors. *Clinical Microbiology Reviews,* 21(4): 583-593 (2008) (hereinafter Daya et al.). Furthermore, in some embodiments, the capsid sequence is a mutant capsid sequence.

AAV Vectors

AAV vectors are derived from adeno-associated virus, which has its name because it was originally described as a contaminant of adenovirus preparations. AAV vectors offer numerous well-known advantages over other types of vectors: wildtype strains infect humans and nonhuman primates without evidence of disease or adverse effects; the AAV capsid displays very low immunogenicity combined with high chemical and physical stability which permits rigorous methods of virus purification and concentration; AAV vector transduction leads to sustained transgene expression in postmitotic, nondividing cells and provides long-term gain of function; and the variety of AAV subtypes and variants offers the possibility to target selected tissues and cell types. Heilbronn R & Weger S, Viral Vectors for Gene Transfer: Current Status of Gene Therapeutics, in M. Schäfer-Korting (ed.), *Drug Delivery,* Handbook of Experimental Pharmacology, 197: 143-170 (2010) (hereinafter Heilbronn). A major limitation of AAV vectors is that the AAV offers only a limited transgene capacity (<4.9 kb) for a conventional vector containing single-stranded DNA.

AAV is a nonenveloped, small, single-stranded DNA-containing virus encapsidated by an icosahedral, 20 nm diameter capsid. The human serotype AAV2 was used in a majority of early studies of AAV. Heilbronn. It contains a 4.7 kb linear, single-stranded DNA genome with two open reading frames rep and cap ("rep" for replication and "cap" for capsid). Rep codes for four overlapping nonstructural proteins: Rep78, Rep68, Rep52, and Rep40. Rep78 and Rep69 are required for most steps of the AAV life cycle, including the initiation of AAV DNA replication at the hairpin-structured inverted terminal repeats (ITRs), which is an essential step for AAV vector production. The cap gene codes for three capsid proteins, VP1, VP2, and VP3. Rep and cap are flanked by 145 bp ITRs. The ITRs contain the origins of DNA replication and the packaging signals, and they serve to mediate chromosomal integration. The ITRs are generally the only AAV elements maintained in AAV vector construction.

To achieve replication, AAVs must be coinfected into the target cell with a helper virus. Grieger J C & Samulski R J, Adeno-associated virus as a gene therapy vector: Vector development, production, and clinical applications. *Adv Biochem Engin/Biotechnol* 99:119-145 (2005). Typically, helper viruses are either adenovirus (Ad) or herpes simplex virus (HSV). In the absence of a helper virus, AAV can establish a latent infection by integrating into a site on human chromosome 19. Ad or HSV infection of cells latently infected with AAV will rescue the integrated genome and begin a productive infection. The four Ad proteins required for helper function are E1A, E1B, E4, and E2A. In addition, synthesis of Ad virus-associated (VA) RNAs is required. Herpesviruses can also serve as helper viruses for productive AAV replication. Genes encoding the helicase-primase complex (UL5, UL8, and UL52) and the DNA-binding protein (UL29) have been found sufficient to mediate the HSV helper effect. In some embodiments of the present invention that employ rAAV vectors, the helper virus is an adenovirus. In other embodiments that employ rAAV vectors, the helper virus is HSV.

Making Recombinant AAV (rAAV) Vectors

The production, purification, and characterization of the rAAV vectors of the present invention may be carried out using any of the many methods known in the art. For reviews of laboratory-scale production methods, see, e.g., Clark R K, Recent advances in recombinant adeno-associated virus vector production. *Kidney Int.* 61s:9-15 (2002); Choi V W et al., Production of recombinant adeno-associated viral vectors for in vitro and in vivo use. *Current Protocols in Molecular Biology* 16.25.1-16.25.24 (2007) (hereinafter Choi et al.); Grieger J C & Samulski R J, Adeno-associated virus as a gene therapy vector: Vector development, production, and clinical applications. *Adv Biochem Engin/Biotechnol* 99:119-145 (2005) (hereinafter Grieger & Samulski); Heilbronn R & Weger S, Viral Vectors for Gene Transfer: Current Status of Gene Therapeutics, in M. Schäfer-Korting (ed.), *Drug Delivery,* Handbook of Experimental Pharmacology, 197: 143-170 (2010) (hereinafter Heilbronn); Howarth J L et al., Using viral vectors as gene transfer tools. *Cell Biol Toxicol* 26:1-10 (2010) (hereinafter Howarth). The production methods described below are intended as non-limiting examples.

AAV vector production may be accomplished by cotransfection of packaging plasmids. Heilbronn. The cell line supplies the deleted AAV genes rep and cap and the required helpervirus functions. The adenovirus helper genes, VA-RNA, E2A and E4 are transfected together with the AAV rep and cap genes, either on two separate plasmids or on a single helper construct. A recombinant AAV vector plasmid wherein the AAV capsid genes are replaced with a transgene expression cassette (comprising the gene of interest, e.g., a CNGB3 nucleic acid; a promoter; and minimal regulatory elements) bracketed by ITRs, is also transfected. These packaging plasmids are typically transfected into 293 cells, a human cell line that constitutively expresses the remaining required Ad helper genes, E1A and E1B. This leads to amplification and packaging of the AAV vector carrying the gene of interest.

Multiple serotypes of AAV, including 12 human serotypes and more than 100 serotypes from nonhuman primates have now been identified. Howarth et al. The AAV vectors of the present invention may comprise capsid sequences derived from AAVs of any known serotype. As used herein, a "known serotype" encompasses capsid mutants that can be produced using methods known in the art. Such methods, include, for example, genetic manipulation of the viral capsid sequence, domain swapping of exposed surfaces of the capsid regions of different serotypes, and generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein. Moreover, the AAV vectors of the present invention may comprise ITRs derived from AAVs of any known serotype. Preferentially, the ITRs are derived from one of the human serotypes AAV1-AAV12. In some embodiments of the present invention, a pseudotyping approach is employed, wherein the genome of one ITR serotype is packaged into a different serotype capsid.

Preferentially, the capsid sequences employed in the present invention are derived from one of the human serotypes AAV1-AAV12. Recombinant AAV vectors containing an AAV5 serotype capsid sequence have been demonstrated to target retinal cells in vivo. See, for example, Komaromy et al. Therefore, in preferred embodiments of the present invention, the serotype of the capsid sequence of the AAV vector is AAV5. In other embodiments, the serotype of the capsid sequence of the AAV vector is AAV1, AAV2, AAV3, AAV4, AAV6, AAV7, AAV8, AAV9, AAV10, AAV11, or AAV12. Even when the serotype of the capsid sequence does not naturally target retinal cells, other methods of specific tissue targeting may be employed. See Howarth et al. For example, recombinant AAV vectors can be directly targeted by genetic manipulation of the viral capsid sequence, particularly in the looped out region of the AAV three-dimensional structure, or by domain swapping of exposed surfaces of the capsid regions of different serotypes, or by generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein.

One possible protocol for the production, purification, and characterization of recombinant AAV (rAAV) vectors is provided in Choi et al. Generally, the following steps are involved: design a transgene expression cassette, design a capsid sequence for targeting a specific receptor, generate adenovirus-free rAAV vectors, purify and titer. These steps are summarized below and described in detail in Choi et al.

The transgene expression cassette may be a single-stranded AAV (ssAAV) vector or a "dimeric" or self-complementary AAV (scAAV) vector that is packaged as a pseudo-double-stranded transgene. Choi et al.; Heilbronn; Howarth. Using a traditional ssAAV vector generally results in a slow onset of gene expression (from days to weeks until a plateau of transgene expression is reached) due to the required conversion of single-stranded AAV DNA into double-stranded DNA. In contrast, scAAV vectors show an onset of gene expression within hours that plateaus within days after transduction of quiescent cells. Heilbronn. However, the packaging capacity of scAAV vectors is approximately half that of traditional ssAAV vectors. Choi et al. Alternatively, the transgene expression cassette may be split between two AAV vectors, which allows delivery of a longer construct. See e.g., Daya et al. A ssAAV vector can be constructed by digesting an appropriate plasmid (such as, for example, a plasmid containing the hCNGB3 gene) with restriction endonucleases to remove the rep and cap fragments, and gel purifying the plasmid backbone containing the AAVwt-ITRs. Choi et al. Subsequently, the desired transgene expression cassette can be inserted between the appropriate restriction sites to construct the single-stranded rAAV vector plasmid. A scAAV vector can be constructed as described in Choi et al.

Then, a large-scale plasmid preparation (at least 1 mg) of the rAAV vector and the suitable AAV helper plasmid and pXX6 Ad helper plasmid can be purified by double CsCl gradient fractionation. Choi et al. A suitable AAV helper plasmid may be selected from the pXR series, pXR1-pXR5, which respectively permit cross-packaging of AAV2 ITR genomes into capsids of AAV serotypes 1 to 5. The appropriate capsid may be chosen based on the efficiency of the capsid's targeting of the cells of interest. For example, in a preferred embodiment of the present invention, the serotype of the capsid sequence of the rAAV vector is AAV5, because this type of capsid is known to effectively target retinal cells. Known methods of varying genome (i.e., transgene expression cassette) length and AAV capsids may be employed to improve expression and/or gene transfer to specific cell types (e.g., retinal cone cells). See, e.g., Yang G S, Virus-mediated transduction of murine retina with adeno-associated virus: Effects of viral capsid and genome size. Journal of Virology, 76(15): 7651-7660.

Next, 293 cells are transfected with pXX6 helper plasmid, rAAV vector plasmid, and AAV helper plasmid. Choi et al. Subsequently the fractionated cell lysates are subjected to a multistep process of rAAV purification, followed by either CsCl gradient purification or heparin sepharose column purification. The production and quantitation of rAAV virions may be determined using a dot-blot assay. In vitro transduction of rAAV in cell culture can be used to verify the infectivity of the virus and functionality of the expression cassette.

In addition to the methods described in Choi et al, various other transfection methods for production of AAV may be used in the context of the present invention. For example, transient transfection methods are available, including methods that rely on a calcium phosphate precipitation protocol.

In addition to the laboratory-scale methods for producing rAAV vectors, the present invention may utilize techniques known in the art for bioreactor-scale manufacturing of AAV vectors, including, for example, Heilbronn; Clement, N. et al. Large-scale adeno-associated viral vector production using a herpesvirus-based system enables manufacturing for clinical studies. Human Gene Therapy, 20: 796-606.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Example 1: Creation and Testing of Shorter Versions of the PR2.1 Promoter

Materials and Methods

Figure 2:
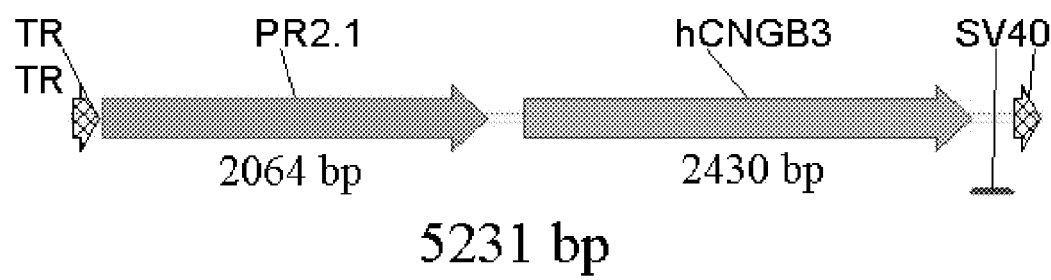
FIG. 2: Schematic drawing of the rAAV5-PR2.1-hCNGB3 vector.

FIG. 2 shows a schematic drawing of the proviral plasmid containing AAV terminal repeats (TR), the PR2.1 promoter and the hCMGB3 transgene. The PR2.1 promoter was shortened by making truncations starting from the 5'-end of PR2.1. The 500 bp core promoter and the 600 bp locus control region (LCR) of PR2.1 were left intact. Three shortened versions of the PR2.1 promoter were created: PR1.7, PR1.5, and PR1.1. PR1.7, PR1.5, and PR1.1 were created by truncating PR2.1 at the 5'-end by approximately 300 bp, 500 bp, and 1,100 bp, respectively.

Figure 3:
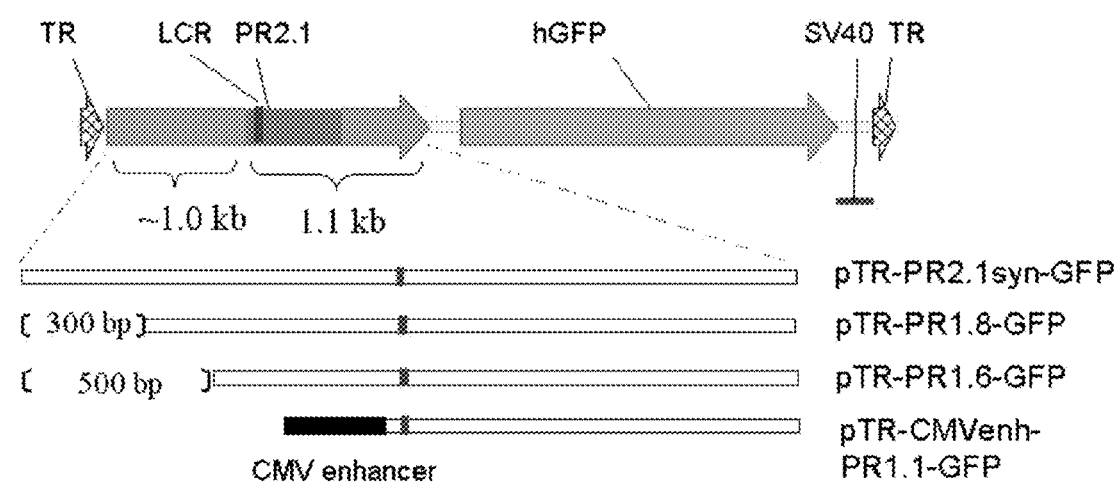
FIG. 3: Schematic drawings of four proviral plasmids that contain variants of the PR2.1 promoter. The PR2.1 promoter (a truncated human red/green opsin promoter) was truncated at its 5'-end by 300 bp, 500 bp, and 1,100 bp to create shorter promoters, designated PR1.7, PR1.5, and PR1.1, respectively. A CMV enhancer was added to the 5' end of the PR1.1 to create a hybrid promoter. The 500 bp core promoter (shown in gray) and the locus control region (shown in red) of PR2.1 were left intact in each of these constructs. Terminal repeats are indicated by the arrows, and the location of SV40 splicing signal sequences is shown.

SEQ ID NO: 1 corresponds to PR1.1 promoter
SEQ ID NO: 2 corresponds to PR1.5 promoter
SEQ ID NO: 3 corresponds to PR1.7 promoter
SEQ ID NO: 4 corresponds to PR2.1 promoter A CMV enhancer was added to the 5' end of the PR1.1 to create a hybrid promoter. Proviral plasmids that contained each of these promoters were created, as shown in FIG. 3. These proviral plasmids (p) contained AAV terminal repeats (TR), a synthesized promoter (PR2.1-syn) or truncations thereof, with or without a CMV enhancer (CMVenh), and a green fluorescent protein (GFP) transgene. The following four proviral plasmids were constructed and sequenced:

(1) pTR-PR2.1syn-GFP
(2) pTR-PR1.8-GFP
(3) pTR-PR1.6-GFP
(4) pTR-CMVenh-PR1.1-GFP.

To construct pTR-PR2.1syn-GFP, a parental plasmid pTR-CMVenh-hGFP was first constructed from pTR-CBA-hRS1 by replacing the CBA and hRS1 sequences with hGFP sequences. The human GFP (hGFP) DNA sequence was PCR amplified from the source with oligonucleotide primers with endonuclease restriction sites at both ends (Not I and BspHI), digested with Not I/BspHI, and joined into pTR-CBA-hRS1 plasmid that had been digested with NotI/NcoI to remove all unnecessary DNA sequences including the chicken beta actin promoter and the hRS1 (but not the CMV enhancer). The resulting plasmid pTR-CMVenh-hGFP contains the CMV enhancer, the hGFP open reading frame (ORF), and the SV40 poly (A) sequence flanked by AAV2 ITRs. The PR2.1 DNA sequence was synthesized according to the DNA sequence 5' of the human red cone opsin (Wang Y. et al., A locus control region adjacent to the human red and green visual pigment genes, Neuron, vol 9, pp 429-440, 1992). The synthesized PR2.1 was composed of bases spanning −4564 to −3009 joined to bases −496 to 0 and contained a LCR essential for expression of both the L and M opsin genes in humans (Komaromy A M et al., Targeting gene expression to cones with human cone opsin promoters in recombinant AAV, Gene Therapy, vol 15, pp 1049-1055, 2008). In addition, a 97 base pair SV40 splice donor/splice acceptor (SD/SA) was attached to the end of PR2.1 promoter. Synthesized PR2.1 including the SD/SA sequence was inserted into the pJ206 cloning vector to generate pJ206-PR2.1 syn. The PR2.1 syn DNA sequence, including the SV40 SD/SA sequence, was released from pJ206-PR2.1 syn by HindIII/Acc65I digestion and inserted into pTR-CMVenh-hGFP that had been digested with HindIII/Acc65I to remove the unnecessary CMV enhancer sequence to generate the plasmid pTR-PR2.1syn-hGFP.

To construct plasmids with shorter versions of the PR2.1 promoter, the PR2.1 sequence with truncation of 300 bp, 500 bp or 1,100 bp from the 5' end of PR2.1 were PCR amplified from pJ206-PR2.1syn. Four oligonucleotide primers were designed:

1) PR right-Hind: 5'-GATTTAAGCTTGCGGCCGCGGG-TACAATTCCGCAGCTTTTAGAG-3' (SEQ ID NO: 5);
2) PR1.1 Left-Hind: 5'-CTGCAAGCTTGTGGGACCA-CAAATCAG-3' (SEQ ID NO: 6);
3) PR1.5 Left-Acc65I: 5'-TAGCGGTACCAGCCATCG-GCTGTTAG-3' (SEQ ID NO: 7); and
4) PR1.7 left-Acc65I: 5'-GTGGGTACCGGAGGCT-GAGGGGTG-3' (SEQ ID NO: 8). Primer PR right-Hind was paired with the other three primers to PCR amplify PR1.1, PR1.5, and PR1.7 respectively. Pfu Ultra HS polymerase mix was used with a thermal cycle of 95° C. for 5 min, and then 35 cycles of 94° C. for 1 min, 58° C. for 45 sec, and 72° C. for 2 min.

PR1.1 was amplified from pJ206-PR2.1syn using the primer set of PR right-Hind and PR1.1-left-Hind. The amplified DNA was digested with HindIII and inserted into pTR-CMVenh-hGFP that had been digested with HindIII to generate plasmid pTR-CMVenh-PR1.1-hGFP.

PR1.5 was amplified from pJ206-PR2.1syn using the primer set of PR right-Hind and PR1.5-left-Acc65I. The amplified DNA was digested with HindIII/Acc65I, and inserted into pTR-CMVenh-hGFP that had been digested with HindIII/Acc65I to generate plasmid pTR-PR1.5-hGFP PR1.7 was amplified from pJ206-PR2.1syn using the primer set of PR right-Hind and PR1.7-left-Acc65I. The amplified DNA was digested with HindIII/Acc65I, and inserted into pTR-CMVenh-hGFP that had been digested with HindIII/Acc65I to generate plasmid pTR-PR1.7-hGFP.

The DNA sequence of the expression cassette, including the promoter and hGFP, were confirmed by DNA sequencing, and the location of TRs was confirmed by SmaI restriction mapping.

To examine if the PR2.1 promoter is functional for RNA transcription and subsequent protein expression, a human retinal pigment epithelia (RPE) cell line, APRE-19, and human embryonic kidney HEK293 cells were seeded in 6-well plates ($5 \times 10^5$ cells/well) and then transfected with 1 μg of DNA from each of six plasmids: pTR-CMVenh-PR1.1-GFP, pTR-PR1.5-GFP, pTR-PR1.7-GFP, pTR-PR2.1syn-GFP, pTR-PR2.1-GFP (Control), or pTR-sm-CBA-GFP (positive control). Transfected cells were incubated at 37° C., 5% CO2 incubator for 4 days. During the period of incubation, transfected cells were examined by fluorescence microscopy for GFP expression.

Results

DNA sequencing and restriction mapping of all four plasmids confirmed that the sequence and the TRs of these proviral plasmids are correct.

In vitro analysis using ARPE-19 and HEK293 cells found that neither of these cell lines supported functionality of the PR2.1 promoter. At 24 h post transfection, strong GFP-expression was observed in cells transfected with DNA from pTR-smCBA-GFP (positive control). At 48 h post transfection, weak GFP expression was observed in cells transfected with DNA from pTR-CMVenh-PR1.1-GFP. No GFP-expressing cells were observed in all other wells, i.e. those transfected with DNA from pTR-PR1.5-GFP, pTR-PR1.7-GFP, pTR-PR2.1syn-GFP, or pTR-PR2.1-GFP. Plasmid pTR-PR2.1-GFP contains the full-length PR2.1 promoter that is known to be functional for RNA transcription and subsequent GFP expression in vivo (Komaromy A M et al., Targeting gene expression to cones with human cone opsin promoters in recombinant AAV, Gene Therapy, vol 15, pp 1049-1055, 2008). Therefore these results indicate that the ARPE-19 cell line does not support PR2.1 promoter, neither any other shorter versions of PR2.1 promoter. Weak expression of GFP from pTR-CMVenh-PR1.1-GFP transfected cells is most likely due to the CMV enhancer, which greatly elevates the strength of the PR1.1 promoter.

Further studies were carried out to evaluate the efficiency and specificity of PR1.1, PR1.5 PR1.7 and PR2.1 to target cones in mice, using rAAV vectors expressing green fluorescent protein (GFP).

Figure 5:
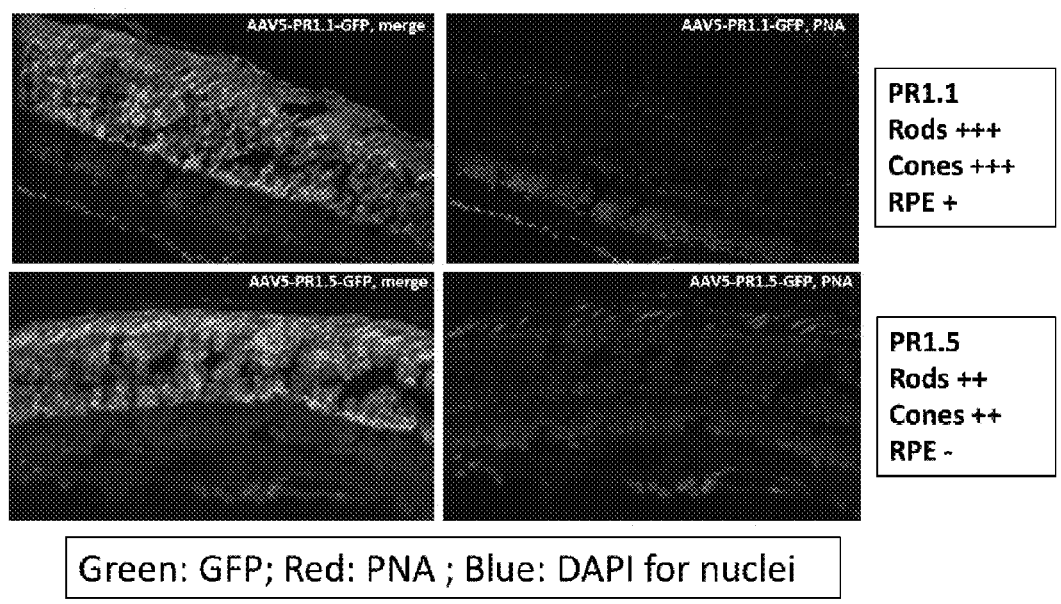
FIG. 5 shows the results of experiments to assess the efficiency and specificity of PR1.1 and PR1.5 to target cones in mice, using rAAV vectors expressing green fluorescent protein (GFP). PNA is a marker for cone photoreceptors. DAPI is used to identify nuclei.
Figure 6:
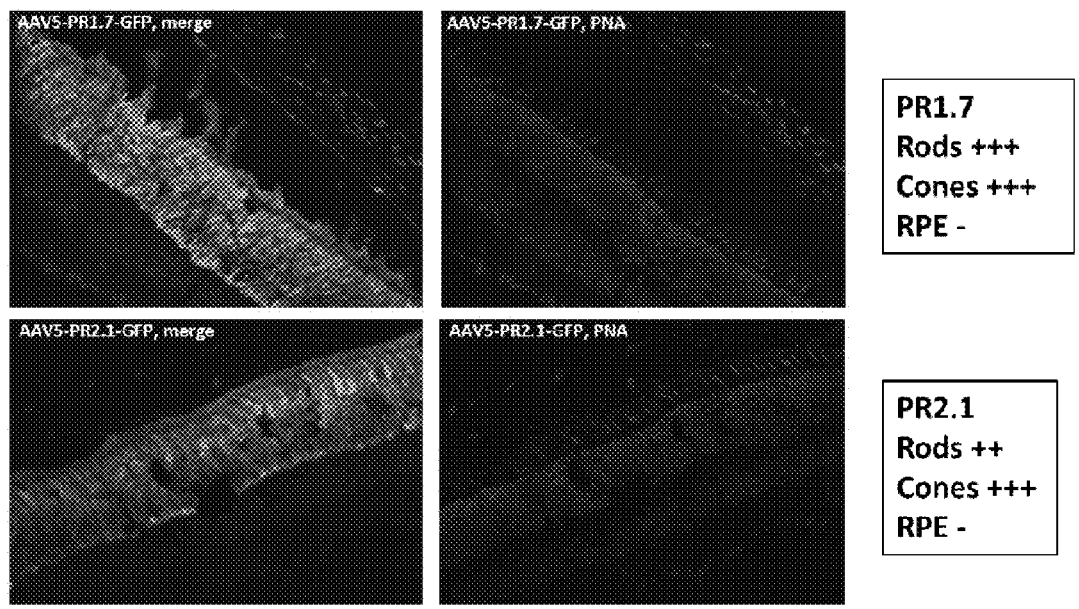
FIG. 6 shows the results of experiments to assess the efficiency and specificity of PR1.7 and PR2.1 to target cones in mice, using rAAV vectors expressing green fluorescent protein (GFP). PNA is a marker for cone photoreceptors. DAPI is used to identify nuclei.

The constructs are packaged in a rAAV capsid and tested in vivo in a mouse model. As shown in FIGS. 5 and 6, four rAAV vectors, i.e. rAAV5-CMVenh-PR1.1-GFP, rAAV5-PR1.5-GFP, rAAV5-PR1.7-GFP, and rAAV5-PR2.1-GFP, are produced by a standard plasmid transfection method. The rAAV vectors that have been packaged in transfected cells are harvested by cell lysis and then purified by iodixanol (IDX) gradient followed by Q Sepharose HP column chromatography, and formulated in Alcon BSS solution. Normal mice are then injected by subretinal injection (1 µL) in both eyes (5 mice per vector). Six weeks post injection, mice are sacrificed, eyes enucleated and retinal sections prepared. Slides are stained with DAPI to identify nuclei and immunostained for GFP and for PNA (a marker for cone photoreceptors). The results are shown in FIGS. 5 and 6. GFP protein expression was detected in photoreceptors (cones and rods) of eyes received rAAV5-GFP vectors containing one of the four promoters, i.e. PR1.1, PR1.5, PR1.7, or PR2.1. In which, PR1.5 is a relatively weaker promoter, and PR1.1 is a strong promoter but has off target GFP expression in RPE cells. Overall, PR1.7 is comparable to the PR2.1 promoter in terms of strength (both score +++ in GFP expression level in cones) and cell type specificity (target to cones and also rods, but not RPE cells).

Example 2: Evaluation in Non-Human Primates

Figure 7:
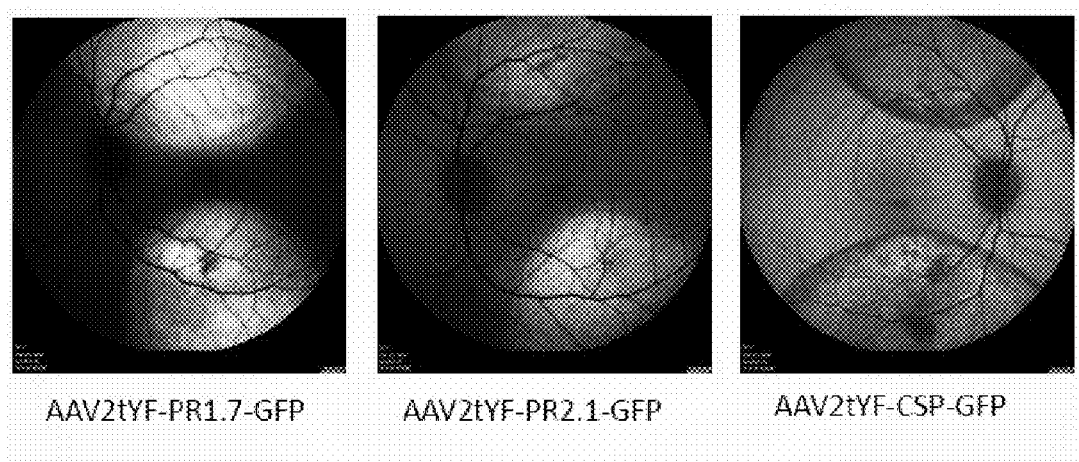
FIG. 7 shows the results of fundus autofluorescence imaging (FAF) to detect the presence of green fluorescent protein (GFP) in the non-human primate (NHP) eyes received subretinally rAAV2tYF-PR2.1-GFP, rAAV2tYF-PR1.7-GFP, or AAV2tYF-CSP-GFP.
Figure 8:
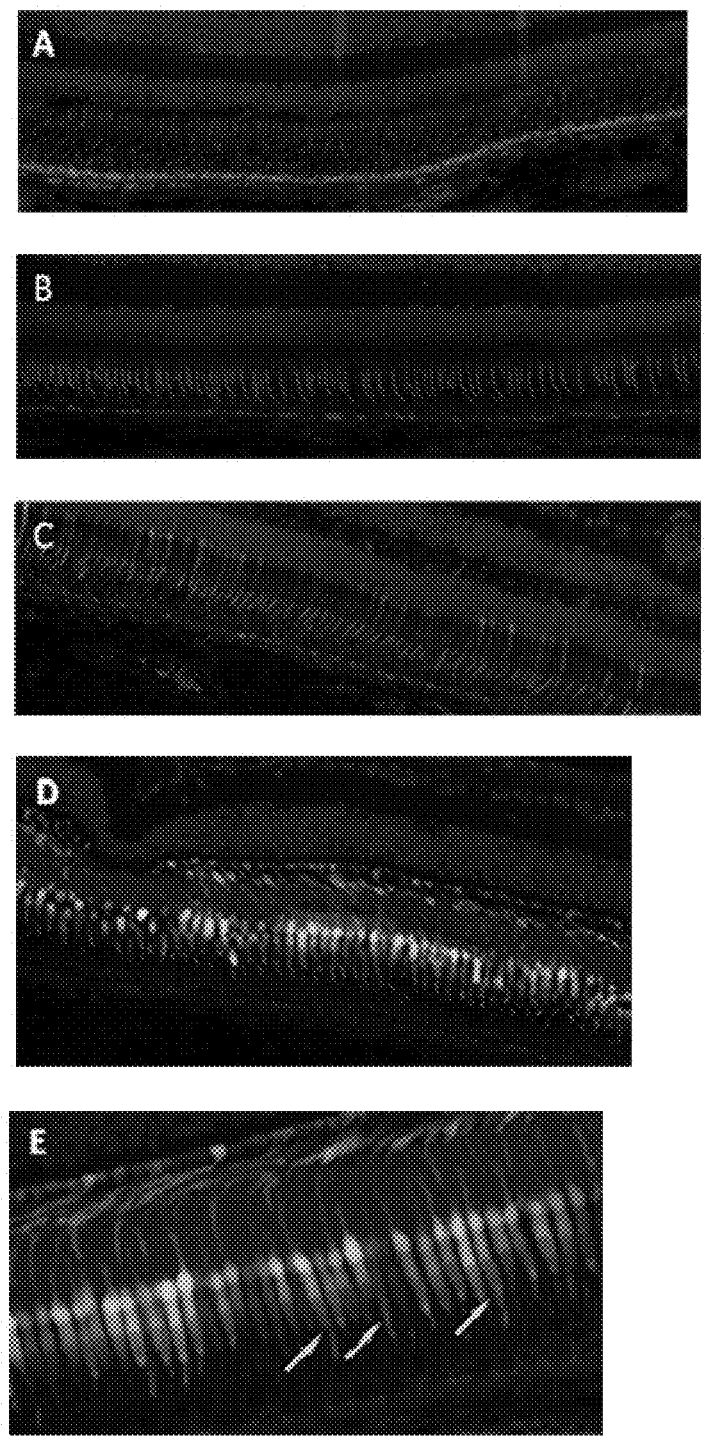
FIG. 8 (A-E) shows GFP expression in NHP retinas 3 months after injection of AAV2tYF-GFP vectors. The panels show representative retinal sections from a normal control eye without AAV treatment (panel A), or from eyes subretinally injected with AAV2tYF-CSP-GFP (panel B), AAV2tYF-PR2.1-GFP (panel C), or AAV2tYF-PR1.7-GFP (panels D & E) stained with DAPI for nuclei (blue) and antibodies to GFP (green), L/M cone opsin (red, panels A, B, C & D) or S cone opsin (red, panel E).
Figure 9:
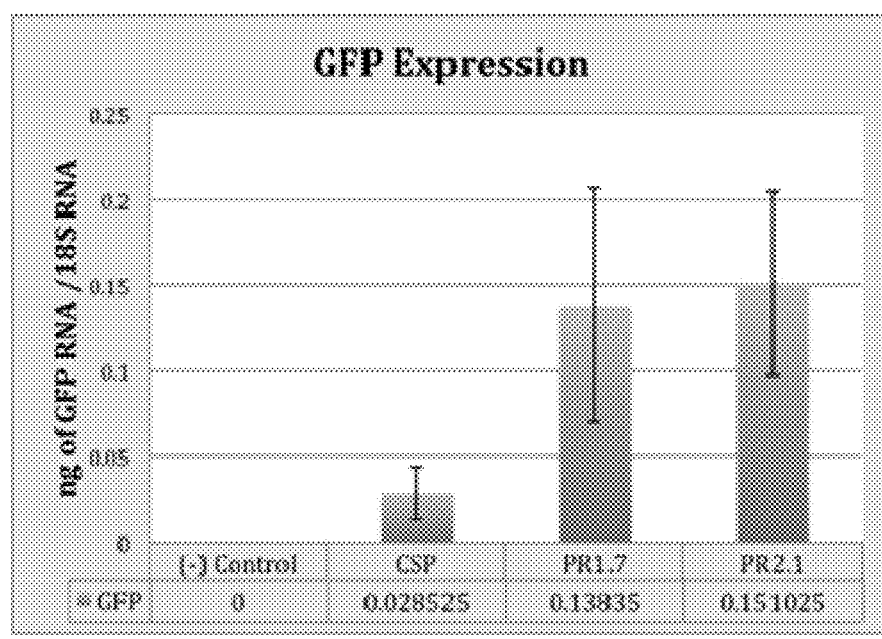
FIG. 9 is a graph that shows levels of message RNA (mRNA) of GFP in NHP retinas 3 months after injection of AAV2tYF-GFP vectors. Message RNA (mRNA) of GFP was determined by qRT-PCR, performed in triplicates at 3 different times, and normalized by 18S RNA expression in samples.

Further studies were carried out to evaluate three cone-specific promoters and three AAV capsid serotypes by comparing their efficiency and specificity to target L, M and S cones in nonhuman primates (NHP), using rAAV vectors expressing green fluorescent protein (GFP). In the first study, six cynomolgus macaques received bilateral subretinal injections of AAV2tYF-GFP containing a PR1.7, CSP, or PR2.1 promoter. Each eye received two injections of 0.1 mL of AAV vector at a concentration of $5 \times 10^{11}$ vg/mL (two 0.05 mL blebs/eye, $1 \times 10^{11}$ vg/eye). Twelve weeks post treatment, retinal tissue was obtained for quantitative reverse transcriptase PCR (qRT-PCR) and immunohistochemistry. The vector with the PR1.7 promoter was found to result in robust and specific targeting of GFP-reporter gene expression (Grade 3) in all three types of cones in the subretinal bleb areas in all NHP eyes. FIG. 7 shows the results of in-life fundus autofluorescence imaging (FAF) to detect the presence of fluorophores (GFP) in the eye. Variable staining of GFP (Grades 0, 1 or 2) was seen in the subretinal bleb areas in the PR2.1 promoter group and no GFP labeling was present in any of the eyes receiving the CSP promoter group (Grade 0) (FIG. 8, Table 1, below). Table 1 is a summary of the herein described Immunohistochemistry Grading in Promoter Selection Study. In Table 1, GFP expression was graded as 0 (no staining), 1 (mild staining), 2 (moderate staining) and 3 (intense staining).

TABLE 1

| Eye | Promoter | R G1 | B1 | R G2 | B2 | Mean | Group Mean | GFP + R G | GFP + B |
|---|---|---|---|---|---|---|---|---|---|
| I00253 OS | None | na | na | 0 | 0 | 0 | 0 | na | na |
| IM080058 OS | None | na | na | 0 | 0 | 0 | | na | na |
| IM083748 OS | None | na | na | 0 | 0 | 0 | | na | na |
| I08050 OS | AAV2tYF-CSP-GFP | 0 | 0 | 0 | 0 | 0 | 0 | no | no |
| I08051 OD | AAV2tYF-CSP-GFP | 0 | 0 | 0 | 0 | 0 | | no | no |
| I08053 OD | AAV2tYF-CSP-GFP | 0 | 0 | 0 | 0 | 0 | | no | no |
| I08054 OS | AAV2tYF-CSP-GFP | 0 | 0 | 0 | 0 | 0 | | no | no |
| I08053 OS | AAV2tYF-PR2.1-GFP | 1 | 1 | 0 | 0 | 0.5 | 1.4 | yes | no |
| I08050 OD | AAV2tYF-PR2.1-GFP | 1 | 2 | 1 | 1 | 1.25 | | yes | yes |
| I08052 OD | AAV2tYF-PR2.1-GFP | 2 | 2 | 1 | 1 | 1.5 | | yes | no |
| I08049 OS | AAV2tYF-PR2.1-GFP | 3 | 2 | 2 | 2 | 2.25 | | yes | yes |
| I08049 OD | AAV2tYF-PR1.7-GFP | 3 | 3 | 3 | 3 | 3 | 3 | yes | yes |
| I08051 OS | AAV2tYF-PR1.7-GFP | 3 | 3 | 3 | 3 | 3 | | yes | yes |
| I08052 OS | AAV2tYF-PR1.7-GFP | 3 | 3 | 3 | 3 | 3 | | yes | yes |
| I08054 OD | AAV2tYF-PR1.7-GFP | 3 | 3 | 3 | 3 | 3 | | yes | yes |

Taken together, the results of these experiments show that the strength and specificity of shortened PR1.7 is comparable to that of PR2.1 in mice. It was found that the PR1.7 promoter directed the highest level of expression ni reg/green and blue cones. The CNGB3 native promoter has been identified to be a strong RPE-specific promoter in mice.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A nucleic acid comprising a cone cell specific promoter PR 2.1, wherein the promoter PR 2.1 comprises the sequence SEQ ID NO: 4.

2. The nucleic acid of claim 1, wherein the promoter is capable of promoting CNGB3 expression in S-cone cells, M-cone cells, and L-cone cells.

3. The nucleic acid of claim 1, wherein the promoter is capable of promoting CNGA3 expression in S-cone cells, M-cone cells, and L-cone cells.

4. The nucleic acid of claim 1, wherein the promoter is capable of promoting GNAT2 expression in S-cone cells, M-cone cells, and L-cone cells.

5. A recombinant adeno-associated (rAAV) expression vector comprising a target nucleic acid sequence operably linked to the nucleic acid of claim 1.

6. The expression vector of claim 5, wherein the target nucleic acid sequence encodes a cyclic nucleotide-gated channel subunit B (CNGB3) polypeptide.

7. The expression vector of claim 5, wherein the target nucleic acid sequence encodes a cyclic nucleotide-gated channel subunit A (CNGA3) polypeptide.

8. The expression vector of claim 7, wherein the CNGA3 is mouse CNGA3.

9. The expression vector of claim 7, wherein the CNGA3 is rat CNGA3.

10. The expression vector of claim 7, wherein the CNGA3 is human CNGA3.

11. The expression vector of claim 5, wherein the target nucleic acid sequence encodes a Guanine nucleotide-binding protein G(t) subunit alpha-2 (GNAT-2) polypeptide.

12. The expression vector of claim 11, wherein the GNAT-2 is mouse GNAT-2.

13. The expression vector of claim 11, wherein the GNAT-2 is rat GNAT-2.

14. The expression vector of claim 11, wherein the GNAT-2 is human GNAT-2.

15. A mammalian cell comprising the expression vector of claim 5.

16. A transgene expression cassette comprising:
(a) the nucleic acid of claim 1;
(b) a nucleic acid selected from the group consisting of a CNGB3 nucleic acid, a CNGA3 nucleic acid, and a GNAT2 nucleic acid; and
(c) minimal regulatory elements.

* * * * *